(12) United States Patent
Valla et al.

(10) Patent No.: US 9,388,421 B2
(45) Date of Patent: Jul. 12, 2016

(54) ENHANCED EXPRESSION METHOD

(75) Inventors: Svein Valla, Trondheim (NO); Rahmi Lale, Trondheim (NO); Laila Berg, Trondheim (NO); Ingrid Bakke, Ranheim (NO)

(73) Assignee: VECTRON BIOSOLUTIONS AS, Trondheim (NO)

( * ) Notice: Subject to any disclaimer, the term of this patent is extended or adjusted under 35 U.S.C. 154(b) by 1206 days.

(21) Appl. No.: 12/376,312

(22) PCT Filed: Aug. 3, 2007

(86) PCT No.: PCT/GB2007/002951
§ 371 (c)(1),
(2), (4) Date: Feb. 4, 2009

(87) PCT Pub. No.: WO2008/015447
PCT Pub. Date: Feb. 7, 2008

(65) Prior Publication Data
US 2010/0248972 A1    Sep. 30, 2010

(30) Foreign Application Priority Data

Aug. 3, 2007 (GB) .................................. 0615556.8

(51) Int. Cl.
*C12N 15/70* (2006.01)
*C07H 21/04* (2006.01)

(52) U.S. Cl.
CPC ...................................... *C12N 15/70* (2013.01)

(58) Field of Classification Search
None
See application file for complete search history.

(56) References Cited

FOREIGN PATENT DOCUMENTS

| WO | 98/08958 A1 | 3/1998 |
|---|---|---|
| WO | 00/68375 A2 | 11/2000 |

OTHER PUBLICATIONS

Pooggins et al, Mol. Gen. Genet., 234:329-331, 1992.*
Gillies et al., Nuc. Acids Res., 16(3):883-893, 1988.*
Ner et al., DNA, 7(2): 127-134, 1988.*
Ohki et al., J. Bacteriol., 186(21): 7450-7455, 2004.*
Fournier et al., J. Bacteriol., 183(7): 2367-2371, 2001.*
Hsu, LM, Promoter clearance and escape in prokaryotes. Biochim Biophys Acta. Sep. 13, 2002; 1577(2):191-207.
Vo, NV et al, In vitro studies of transcript initiation by *Escherichia coli* RNA polymerase. 3. Influences of individual DNA elements within the promoter recognition region on abortive initiation and promoter escape. Biochemistry. Apr. 8, 2003; 42(13):3798-811.
de Smit, MH et al, Control of translation by mRNA secondary structure in *Escherichia coli*. A quantitative analysis of literature data. J Mol Biol. Nov. 25, 1994;244(2):144-50.
Kozak, M, Initiation of translation in prokaryotes and eukaryotes. Gene. Jul. 8, 1999; 234(2):187-208.
Komarova, Av et al, Au-rich sequences within 5' untranslated leaders enhance translation and stabilize mRNA in *Escherichia coli*. J Bacteriol. Feb. 2005; 187(4):1344-9.
Coleman, J et al, Mutations upstream of the ribosome-binding site affect translational efficiency. J Mol Biol. Jan. 5, 1985; 181(1):139-43.
Inouye, S et al, Nucleotide sequence of the promoter region of the xylDEGF operon on TOL plasmid of Pseudomonas putida. Gene. Sep. 1984; 29(3):323-30.
Winther-Larsen, HC et al, Pm promoter expression mutants and their use in broad-host-range RK2 plasmid vectors. Metab Eng. Apr. 2000; 2(2):92-103.
Dobrynin, VN et al, Synthesis of a model promoter for gene expression in *Escherichia coli*. Nucleic Acids Symp Ser. 1980; (7):365-76.
Adhin, MR et al, Scanning model for translational reinitiation in eubacteria. J Mol Biol. Jun. 20, 1990; 213(4):811-8.
Uhlin, BE et al, R plasmid gene dosage effects in *Escherichia coli* K-12: copy mutants of the R plasmid R1drd-19. Plasmid. Nov. 1977; 1(1):1-7.
Chervaux, C et al, Secretion of active beta-lactamase to the medium mediated by the *Escherichia coli* haemolysin transport pathway. Mol Gen Genet. Nov. 15, 1995; 249(2):237-45.
Blatny, JM et al, Construction and use of a versatile set of broad-host-range cloning and expression vectors based on the RK2 replicon. Appl Environ Microbiol. Feb. 1997; 63(2):370-9.
Sletta, H et al, Broad-host-range plasmid pJB658 can be used for industrial-level production of a secreted host-toxic single-chain antibody fragment in *Escherichia coli*. Appl Environ Microbiol. Dec. 2004; 70(12):7033-9.
Andrè, A et al, Reinitiation of protein synthesis in *Escherichia coli* can be induced by mRNA cis-elements unrelated to canonical translation initiation signals. FEBS Lett. Feb. 18, 2000; 468(1):73-8.
Schäfer, A et al, Small mobilizable multi-purpose cloning vectors derived from the *Escherichia coli* plasmids pK18 and pK19: selection of defined deletions in the chromosome of Corynebacterium glutamicum. Gene. Jul. 22, 1994; 145 (1):69-73.
Lopez, PJ et al, The use of a tRNA as a transcriptional reporter: the T7 late promoter is extremely efficient in *Escherichia coli* but its transcripts are poorly expressed. Nucleic Acids Res. Apr. 11, 1994;22(7):1186-93. Erratum in: Nucleic Acids Res. Jun. 25, 1994; 22(12):2434.
Fjærvik, E et al, Complementation of cellulose-negative mutants of Acetobacter xylinum by the cloned structural gene for phosphoglucomutase. FEMS Microbiol. Letts 1991; 77(2-3): 325-330.
Castán, P et al, Multiple regulatory mechanisms act on the 5' untranslated region of the S-layer gene from Thermus thermophilus HB8. J Bacteriol. Feb. 2001; 183(4):1491-4.

(Continued)

*Primary Examiner* — Nancy T Vogel
(74) *Attorney, Agent, or Firm* — Porter, Wright, Morris & Arthur LLP

(57) ABSTRACT

The present invention concerns a method of producing a desired heterologous gene product wherein said heterologous gene product is expressed from a strong promoter, said method comprising expressing said gene using a mutant mRNA leader which comprises one or more mutations which enhance transcription of the gene. The invention also provides a mutant Pm mRNA leader sequence, and a vector and a library comprising the leader sequence. Methods of obtaining an mRNA mutant leader and identifying an mRNA mutant leader are encompassed, along with a vector for selection or identification of an mRNA leader mutant and a use thereof for screening.

12 Claims, 6 Drawing Sheets

(56) References Cited

OTHER PUBLICATIONS

Figure 1:
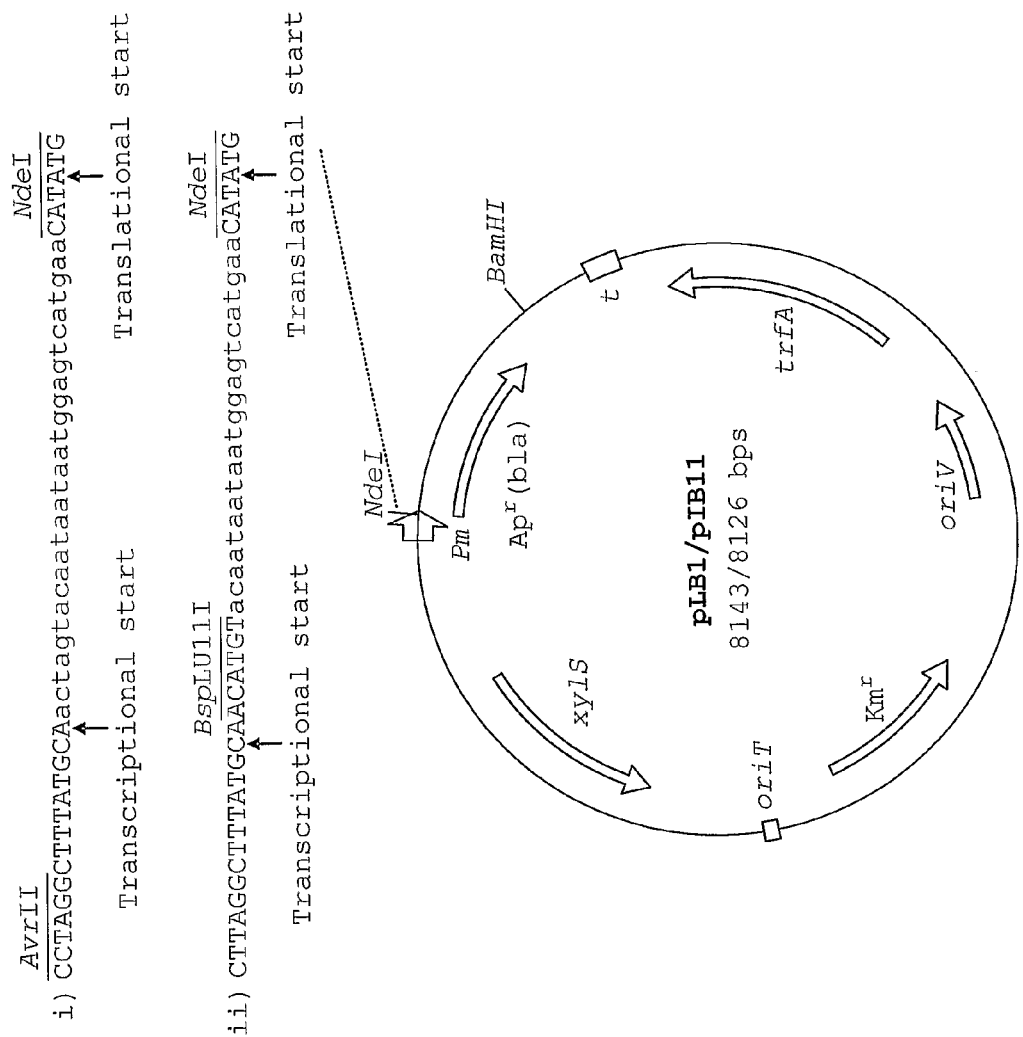

Blatny, JM et al, Improved broad-host-range RK2 vectors useful for high and low regulated gene expression levels in gram-negative bacteria. Plasmid. 1997; 38(1):35-51.

Database Geneseq. Plasmid pJT19bla synthetic oligonucleotide. Database accession No. AAC83761; 2001.

Komine, Y et al, Genomic organization and physical mapping of the transfer RNA genes in *Escherichia coli* K12. J Mol Biol. Apr. 20, 1990; 212(4):579-98.

Kammerer, W et al, Functional dissection of *Escherichia coli* promoters: information in the transcribed region is involved in late steps of the overall process. Embo J. Nov. 1986;5(11):2995-3000. PMID: 3539590 [PubMed].

Boyen, A et al, Enhancement of translation efficiency in *Escherichia coli* by mutations in a proximal domain of messenger RNA. J Mol Biol. Dec. 15, 1982; 162(3):715-20.

Komarova, AV et al, Protein S1 counteracts the inhibitory effect of the extended Shine-Dalgarno sequence on translation. RNA. Sep. 2002;8(9):1137-47.

Olins, PO et al, The T7 phage gene 10 leader RNA, a ribosome-binding site that dramatically enhances the expression of foreign genes in *Escherichia coli*. Gene. Dec. 15, 1988; 73(1):227-35.

Hu, MC et al, rRNA-complementarity in the 5' untranslated region of mRNA specifying the Gtx homeodomain protein: evidence that base-pairing to 18S rRNA affects translational efficiency. Proc Natl Acad Sci U S A. Feb. 16, 1999;96 (4):1339-44.

Ringquist, S et al, Translation initiation in *Escherichia coli*: sequences within the ribosome-binding site. Mol Microbiol. May 1992; 6(9):1219-29.

Wells, DR et al, HSP101 functions as a specific translational regulatory protein whose activity is regulated by nutrient status. Genes Dev. Oct. 15, 1998; 12(20):3236-51.

Boni, IV et al, Ribosome-messenger recognition: mRNA target sites for ribosomal protein S1. Nucleic Acids Res. Jan. 11, 1991; 19(1):155-62.

McCarthy, JE et al, Enhancement of translational efficiency by the *Escherichia coli* atpE translational initiation region: its fusion with two human genes. Gene. 1986;41(2-3):201-6.

McCarthy, JE et al, Translational initiation frequency of atp genes from *Escherichia coli*: identification of an intercistronic sequence that enhances translation. Embo J. Feb. 1985;4(2):519-26.

Schauder, B et al, Inducible expression vectors incorporating the *Escherichia coli* atpE translational initiation region. Gene. 1987; 52(2-3):279-83.

O'Connor, M et al, Enhancement of translation by the epsilon element is independent of the sequence of the 460 region of 16S rRNA. Nucleic Acids Res. Apr. 1, 2001; 29(7):1420-5.

Walker, KA et al, Factors affecting start site selection at the *Escherichia coli* fis promoter. J Bacteriol. Sep. 2002; 184(17):4783-91.

Hsu, LM et al, In vitro studies of transcript initiation by *Escherichia coli* RNA polymerase. 1. RNA chain initiation, abortive initiation, and promoter escape at three bacteriophage promoters. Biochemistry 2003; 42:3777-3786.

Kubori, T et al, A branched pathway in the early stage of transcription by *Escherichia coli* RNA polymerase. J Mol Biol. Mar. 1, 1996; 256(3):449-57.

Ramos, JL et al, Transcriptional control of the Pseudomonas TOL plasmid catabolic operons is achieved through an interplay of host factors and plasmid-encoded regulators. Annu Rev Microbiol. 1997; 51:341-73.

Lewis, DE et al, Axiom of determining transcription start points by RNA polymerase in *Escherichia coli*. Mol Microbiol. Nov. 2004; 54(3):692-701.

Collins, CH et al, Directed evolution of Vibrio fischeri LuxR for increased sensitivity to a broad spectrum of acyl-homoserine lactones. Mol Microbiol. Feb. 2005;55(3):712-23.

Vo, NV et al, In Vitro Studies of Transcript Initiation by *Escherichia coli* RNA Polymerase. 2. Formation and Characterization of Two Distinct Classes of Initial Transcribing Complexes. Biochemistry 2003; 42: 3787-3797.

* cited by examiner

SEQUENCE LISTING

<160> NUMBER OF SEQ ID NOS: 86

<210> SEQ ID NO 1
<211> LENGTH: 35
<212> TYPE: DNA
<213> ORGANISM: Artificial
<220> FEATURE:
<223> OTHER INFORMATION: Pm UTR

<400> SEQUENCE: 1
aactagtaca ataataatgg agtcatgaac atatg                            35

<210> SEQ ID NO 2
<211> LENGTH: 35
<212> TYPE: DNA
<213> ORGANISM: Artificial
<220> FEATURE:
<223> OTHER INFORMATION: mutant Pm UTR

<400> SEQUENCE: 2
aactagtata acactaatgg agccatgaac atatg                            35

<210> SEQ ID NO 3
<211> LENGTH: 35
<212> TYPE: DNA
<213> ORGANISM: Artificial
<220> FEATURE:
<223> OTHER INFORMATION: mutant Pm UTR

<400> SEQUENCE: 3
acatagtaca ttaatattgg agtcatgaac atatg                            35

<210> SEQ ID NO 4
<211> LENGTH: 35
<212> TYPE: DNA
<213> ORGANISM: Artificial
<220> FEATURE:
<223> OTHER INFORMATION: mutant Pm UTR

<400> SEQUENCE: 4
acattgtact ataatgatgg agtcatgaac atatg                            35

<210> SEQ ID NO 5
<211> LENGTH: 35
<212> TYPE: DNA
<213> ORGANISM: Artificial
<220> FEATURE:
<223> OTHER INFORMATION: mutant Pm UTR

<400> SEQUENCE: 5
atatagtaca acaatactgg agtcatgaac atatg                            35

<210> SEQ ID NO 6
<211> LENGTH: 35
<212> TYPE: DNA
<213> ORGANISM: Artificial
<220> FEATURE:
<223> OTHER INFORMATION: mutant Pm UTR

<400> SEQUENCE: 6
atatactaca acattaatgg agtcatgaac atatg                            35

<210> SEQ ID NO 7
<211> LENGTH: 35
<212> TYPE: DNA
<213> ORGANISM: Artificial
<220> FEATURE:
<223> OTHER INFORMATION: mutant Pm UTR

<400> SEQUENCE: 7
aaattgtacc ataatactgg agtcatgaac atatg                            35

<210> SEQ ID NO 8
<211> LENGTH: 35

```
<212> TYPE: DNA
<213> ORGANISM: Artificial
<220> FEATURE:
<223> OTHER INFORMATION: mutant Pm UTR

<400> SEQUENCE: 8
atctagtata acataaatgg agtcatgaac atatg                              35

<210> SEQ ID NO 9
<211> LENGTH: 35
<212> TYPE: DNA
<213> ORGANISM: Artificial
<220> FEATURE:
<223> OTHER INFORMATION: mutant Pm UTR

<400> SEQUENCE: 9
acatagtaca atattaatgg agtcatgaac atatg                              35

<210> SEQ ID NO 10
<211> LENGTH: 35
<212> TYPE: DNA
<213> ORGANISM: Artificial
<220> FEATURE:
<223> OTHER INFORMATION: mutant Pm UTR

<400> SEQUENCE: 10
atctagtgta acataaatgg agtcatgaac atatg                              35

<210> SEQ ID NO 11
<211> LENGTH: 35
<212> TYPE: DNA
<213> ORGANISM: Artificial
<220> FEATURE:
<223> OTHER INFORMATION: mutant Pm UTR

<400> SEQUENCE: 11
aaatagtacc acactaatgg agtcatgaac atatg                              35

<210> SEQ ID NO 12
<211> LENGTH: 35
<212> TYPE: DNA
<213> ORGANISM: Artificial
<220> FEATURE:
<223> OTHER INFORMATION: mutant Pm UTR

<400> SEQUENCE: 12
aaatagtaca ctactaatgg agtaatgaac atatg                              35

<210> SEQ ID NO 13
<211> LENGTH: 35
<212> TYPE: DNA
<213> ORGANISM: Artificial
<220> FEATURE:
<223> OTHER INFORMATION: mutant Pm UTR

<400> SEQUENCE: 13
aacatgtaca ataataatgg agtcatgaac atatg                              35

<210> SEQ ID NO 14
<211> LENGTH: 35
<212> TYPE: DNA
<213> ORGANISM: Artificial
<220> FEATURE:
<223> OTHER INFORMATION: mutant Pm UTR

<400> SEQUENCE: 14
```
aacatgtacc ataataaagg agtcttgaac atatg        35

<210> SEQ ID NO 15
<211> LENGTH: 35
<212> TYPE: DNA
<213> ORGANISM: Artificial
<220> FEATURE:
<223> OTHER INFORMATION: mutant Pm UTR

<400> SEQUENCE: 15
aacatgtacc ataataatgg agttttgaac atatg        35

<210> SEQ ID NO 16
<211> LENGTH: 35
<212> TYPE: DNA
<213> ORGANISM: Artificial
<220> FEATURE:
<223> OTHER INFORMATION: mutant Pm UTR

<400> SEQUENCE: 16
aacatgtacc atattaatgg agtcttgaac atatg        35

<210> SEQ ID NO 17
<211> LENGTH: 35
<212> TYPE: DNA
<213> ORGANISM: Artificial
<220> FEATURE:
<223> OTHER INFORMATION: mutant Pm UTR

<400> SEQUENCE: 17
aacatgtacc ataataatgg agtaatgaac atatg        35

<210> SEQ ID NO 18
<211> LENGTH: 35
<212> TYPE: DNA
<213> ORGANISM: Artificial
<220> FEATURE:
<223> OTHER INFORMATION: mutant Pm UTR

<400> SEQUENCE: 18
aacatgtcaa acactaatgg agtaatgaac atatg        35

<210> SEQ ID NO 19
<211> LENGTH: 35
<212> TYPE: DNA
<213> ORGANISM: Artificial
<220> FEATURE:
<223> OTHER INFORMATION: mutant Pm UTR

<400> SEQUENCE: 19
aacatgtaac ataataatgg agtcttgaac atatg        35

<210> SEQ ID NO 20
<211> LENGTH: 35
<212> TYPE: DNA
<213> ORGANISM: Artificial
<220> FEATURE:
<223> OTHER INFORMATION: mutant Pm UTR

<400> SEQUENCE: 20
aacatgtaac ataatactgg agtaatgaac atatg        35

<210> SEQ ID NO 21
<211> LENGTH: 35
<212> TYPE: DNA
<213> ORGANISM: Artificial

<220> FEATURE:
<223> OTHER INFORMATION: mutant Pm UTR

<400> SEQUENCE: 21
aacatgtacc acaataatgg agtcttgaac atatg          35

<210> SEQ ID NO 22
<211> LENGTH: 35
<212> TYPE: DNA
<213> ORGANISM: Artificial
<220> FEATURE:
<223> OTHER INFORMATION: mutant Pm UTR

<400> SEQUENCE: 22
aacatgtaca atcatacagg agtcatcaac atatg          35

<210> SEQ ID NO 23
<211> LENGTH: 35
<212> TYPE: DNA
<213> ORGANISM: Artificial
<220> FEATURE:
<223> OTHER INFORMATION: mutant Pm UTR

<400> SEQUENCE: 23
aacatgtacc acaataatgg agttttgaac atatg          35

<210> SEQ ID NO 24
<211> LENGTH: 35
<212> TYPE: DNA
<213> ORGANISM: Artificial
<220> FEATURE:
<223> OTHER INFORMATION: mutant Pm UTR

<400> SEQUENCE: 24
aacatgttac acaataatgg agtaatgaac atatg          35

<210> SEQ ID NO 25
<211> LENGTH: 33
<212> TYPE: DNA
<213> ORGANISM: Artificial
<220> FEATURE:
<223> OTHER INFORMATION: mutant Pm UTR

<400> SEQUENCE: 25
aacatgtcca ataataatgg agtataacat atg          33

<210> SEQ ID NO 26
<211> LENGTH: 35
<212> TYPE: DNA
<213> ORGANISM: Artificial
<220> FEATURE:
<223> OTHER INFORMATION: mutant Pm UTR

<400> SEQUENCE: 26
aacatgtccc attatactgg agtcttgaac atatg          35

<210> SEQ ID NO 27
<211> LENGTH: 35
<212> TYPE: DNA
<213> ORGANISM: Artificial
<220> FEATURE:
<223> OTHER INFORMATION: mutant Pm UTR

<400> SEQUENCE: 27
aacatgtacc ataataatgg agtcctgaac atatg          35

<210> SEQ ID NO 28
<211> LENGTH: 35
<212> TYPE: DNA
<213> ORGANISM: Artificial
<220> FEATURE:
<223> OTHER INFORMATION: mutant Pm UTR

<400> SEQUENCE: 28
aacatgtacc atattaatgg agttatgaac atatg           35

<210> SEQ ID NO 29
<211> LENGTH: 35
<212> TYPE: DNA
<213> ORGANISM: Artificial
<220> FEATURE:
<223> OTHER INFORMATION: mutant Pm UTR

<400> SEQUENCE: 29
aacatgtacc ataataatgg agtcttgaac atatg           35

<210> SEQ ID NO 30
<211> LENGTH: 36
<212> TYPE: DNA
<213> ORGANISM: Artificial
<220> FEATURE:
<223> OTHER INFORMATION: mutant Pm UTR

<400> SEQUENCE: 30
aacatgtact ataataatcg aggtcatgaa catatg          36

<210> SEQ ID NO 31
<211> LENGTH: 36
<212> TYPE: DNA
<213> ORGANISM: Artificial
<220> FEATURE:
<223> OTHER INFORMATION: mutant Pm UTR

<400> SEQUENCE: 31
aacatgttac aataattttg gagccatgaa catatg          36

<210> SEQ ID NO 32
<211> LENGTH: 35
<212> TYPE: DNA
<213> ORGANISM: Artificial
<220> FEATURE:
<223> OTHER INFORMATION: mutant Pm UTR

<400> SEQUENCE: 32
aacatgtaca ataatacacg agtcatgaac atatg           35

<210> SEQ ID NO 33
<211> LENGTH: 35
<212> TYPE: DNA
<213> ORGANISM: Artificial
<220> FEATURE:
<223> OTHER INFORMATION: mutant Pm UTR

<400> SEQUENCE: 33
aacatgtcca agtatacagg agtcatgaac atatg           35

<210> SEQ ID NO 34
<211> LENGTH: 35
<212> TYPE: DNA
<213> ORGANISM: Artificial
<220> FEATURE:
<223> OTHER INFORMATION: mutant Pm UTR

```
<400> SEQUENCE: 34
aacatgtacc attataacgg agtaatgaac atatg                               35

<210> SEQ ID NO 35
<211> LENGTH: 35
<212> TYPE: DNA
<213> ORGANISM: Artificial
<220> FEATURE:
<223> OTHER INFORMATION: mutant Pm UTR

<400> SEQUENCE: 35
aacatgtacc ataatacagg agttatgaac atatg                               35

<210> SEQ ID NO 36
<211> LENGTH: 35
<212> TYPE: DNA
<213> ORGANISM: Artificial
<220> FEATURE:
<223> OTHER INFORMATION: mutant Pm UTR

<400> SEQUENCE: 36
aacatgtaca ataatacagg aacaatgaac atatg                               35

<210> SEQ ID NO 37
<211> LENGTH: 35
<212> TYPE: DNA
<213> ORGANISM: Artificial
<220> FEATURE:
<223> OTHER INFORMATION: mutant Pm UTR

<400> SEQUENCE: 37
aacatgtaca atcataccag agtaatgcca atatg                               35

<210> SEQ ID NO 38
<211> LENGTH: 10
<212> TYPE: RNA
<213> ORGANISM: Artificial
<220> FEATURE:
<223> OTHER INFORMATION: AU rich tract

<400> SEQUENCE: 38
aaggagguga                                                           10

<210> SEQ ID NO 39
<211> LENGTH: 8
<212> TYPE: RNA
<213> ORGANISM: Artificial
<220> FEATURE:
<223> OTHER INFORMATION: AU rich tract

<400> SEQUENCE: 39 aaggaggu                                                              8

<210> SEQ ID NO 40
<211> LENGTH: 6
<212> TYPE: RNA
<213> ORGANISM: Artificial
<220> FEATURE:
<223> OTHER INFORMATION: AU rich tract

<400> SEQUENCE: 40 aaggag                                                                6

<210> SEQ ID NO 41
```

```
<211> LENGTH: 4
<212> TYPE: RNA
<213> ORGANISM: Artificial
<220> FEATURE:
<223> OTHER INFORMATION: Shine Dalgarno sequence

<400> SEQUENCE: 41 ggag                                                                      4

<210> SEQ ID NO 42
<211> LENGTH: 4
<212> TYPE: RNA
<213> ORGANISM: Artificial
<220> FEATURE:
<223> OTHER INFORMATION: Shine Dalgarno sequence

<400> SEQUENCE: 42 agga                                                                      4

<210> SEQ ID NO 43
<211> LENGTH: 33
<212> TYPE: DNA
<213> ORGANISM: Artificial
<220> FEATURE:
<223> OTHER INFORMATION: primer

<400> SEQUENCE: 43
gaaaggccta ccccctaggc tttatgcaac tag                                     33

<210> SEQ ID NO 44
<211> LENGTH: 33
<212> TYPE: DNA
<213> ORGANISM: Artificial
<220> FEATURE:
<223> OTHER INFORMATION: primer

<400> SEQUENCE: 44
ctagttgcat aaagcctagg gggtaggcct ttc                                     33

<210> SEQ ID NO 45
<211> LENGTH: 29
<212> TYPE: DNA
<213> ORGANISM: Artificial
<220> FEATURE:
<223> OTHER INFORMATION: primer

<400> SEQUENCE: 45
catgtacaat aataatggag tcatgaaca                                          29

<210> SEQ ID NO 46
<211> LENGTH: 27
<212> TYPE: DNA
<213> ORGANISM: Artificial
<220> FEATURE:
<223> OTHER INFORMATION: primer

<400> SEQUENCE: 46
tatgttcatg actccattat tattgta                                            27

<210> SEQ ID NO 47
<211> LENGTH: 29
<212> TYPE: DNA
<213> ORGANISM: Artificial
<220> FEATURE:
<223> OTHER INFORMATION: primer

<400> SEQUENCE: 47
```
agcctatgcc tagatcttcc agggtgacg          29

<210> SEQ ID NO 48
<211> LENGTH: 27
<212> TYPE: DNA
<213> ORGANISM: Artificial
<220> FEATURE:
<223> OTHER INFORMATION: primer

<400> SEQUENCE: 48
tatcatcgat aacatgtaat gcggtag            27

<210> SEQ ID NO 49
<211> LENGTH: 70
<212> TYPE: DNA
<213> ORGANISM: Artificial
<220> FEATURE:
<223> OTHER INFORMATION: primer

<400> SEQUENCE: 49
tcatgaacat atgttatttc tctttcttaa aaatatttaa ttaaataatg agtattcaac     60
atttccgtgt                               70

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
agctagagga tccccgggta                    20

<210> SEQ ID NO 51
<211> LENGTH: 23
<212> TYPE: DNA
<213> ORGANISM: Artificial
<220> FEATURE:
<223> OTHER INFORMATION: primer

<400> SEQUENCE: 51
tcatgaacat atggaagacg cca                23

<210> SEQ ID NO 52
<211> LENGTH: 30
<212> TYPE: DNA
<213> ORGANISM: Artificial
<220> FEATURE:
<223> OTHER INFORMATION: primer

<400> SEQUENCE: 52
gctgaataca ttaattaaat acaatttgga         30

<210> SEQ ID NO 53
<211> LENGTH: 26
<212> TYPE: DNA
<213> ORGANISM: Artificial
<220> FEATURE:
<223> OTHER INFORMATION: primer

<400> SEQUENCE: 53
gagtcatgaa catatgccca gcataa             26

<210> SEQ ID NO 54

```
<211> LENGTH: 30
<212> TYPE: DNA
<213> ORGANISM: Artificial
<220> FEATURE:
<223> OTHER INFORMATION: primer

<400> SEQUENCE: 54
atggaatcat ttaattaaat agccagcgtt                                         30

<210> SEQ ID NO 55
<211> LENGTH: 42
<212> TYPE: DNA
<213> ORGANISM: Artificial
<220> FEATURE:
<223> OTHER INFORMATION: oligonucleotide

<400> SEQUENCE: 55
tatgttcatg actccattat tattgtacta gttgcataaa gc                           42

<210> SEQ ID NO 56
<211> LENGTH: 16
<212> TYPE: DNA
<213> ORGANISM: Artificial
<220> FEATURE:
<223> OTHER INFORMATION: oligonucleotide

<400> SEQUENCE: 56
ctaggcttta tgcaca                                                        16

<210> SEQ ID NO 57
<211> LENGTH: 27
<212> TYPE: DNA
<213> ORGANISM: Artificial
<220> FEATURE:
<223> OTHER INFORMATION: oligonucleotide

<400> SEQUENCE: 57
tatgttcatg actccattat tattgta                                            27

<210> SEQ ID NO 58
<211> LENGTH: 7
<212> TYPE: DNA
<213> ORGANISM: Artificial
<220> FEATURE:
<223> OTHER INFORMATION: oligonucleotide

<400> SEQUENCE: 58 catgtca                                                                   7

<210> SEQ ID NO 59
<211> LENGTH: 33
<212> TYPE: DNA
<213> ORGANISM: Artificial
<220> FEATURE:
<223> OTHER INFORMATION: primer

<400> SEQUENCE: 59
ctatcaaacc ggacacgttt atcgtggtta tgc                                     33

<210> SEQ ID NO 60
<211> LENGTH: 22
<212> TYPE: DNA
<213> ORGANISM: Artificial
<220> FEATURE:
<223> OTHER INFORMATION: primer

<400> SEQUENCE: 60
```
ctttcaccag cgtttctggg tg                                    22

<210> SEQ ID NO 61
<211> LENGTH: 21
<212> TYPE: DNA
<213> ORGANISM: Artificial
<220> FEATURE:
<223> OTHER INFORMATION: primer

<400> SEQUENCE: 61
gatgtagaaa ggcgccaagt c                                     21

<210> SEQ ID NO 62
<211> LENGTH: 21
<212> TYPE: DNA
<213> ORGANISM: Artificial
<220> FEATURE:
<223> OTHER INFORMATION: primer

<400> SEQUENCE: 62
gatgtagaaa ggcgccaagt c                                     21

<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
ttcgaagtat tccgcgtacg tg                                    22

<210> SEQ ID NO 64
<211> LENGTH: 21
<212> TYPE: DNA
<213> ORGANISM: Artificial
<220> FEATURE:
<223> OTHER INFORMATION: primer

<400> SEQUENCE: 64
gatgtagaaa ggcgccaagt c                                     21

<210> SEQ ID NO 65
<211> LENGTH: 22
<212> TYPE: DNA
<213> ORGANISM: Artificial
<220> FEATURE:
<223> OTHER INFORMATION: primer

<400> SEQUENCE: 65
tggtcagcga ggaaccacga tg                                    22

<210> SEQ ID NO 66
<211> LENGTH: 23
<212> TYPE: DNA
<213> ORGANISM: Artificial
<220> FEATURE:
<223> OTHER INFORMATION: primer

<400> SEQUENCE: 66
acgttttcca atgatgagca ctt                                   23

<210> SEQ ID NO 67
<211> LENGTH: 16
<212> TYPE: DNA

<213> ORGANISM: Artificial
<220> FEATURE:
<223> OTHER INFORMATION: primer

<400> SEQUENCE: 67
tgcccggcgt caacac                                                        16

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
cggcgccatt ctatcctcta                                                    20

<210> SEQ ID NO 69
<211> LENGTH: 25
<212> TYPE: DNA
<213> ORGANISM: Artificial
<220> FEATURE:
<223> OTHER INFORMATION: primer

<400> SEQUENCE: 69
agggcgtatc tcttcatagc cttat                                              25

<210> SEQ ID NO 70
<211> LENGTH: 23
<212> TYPE: DNA
<213> ORGANISM: Artificial
<220> FEATURE:
<223> OTHER INFORMATION: primer

<400> SEQUENCE: 70
accagcttca atgaaaacca cat                                                23

<210> SEQ ID NO 71
<211> LENGTH: 17
<212> TYPE: DNA
<213> ORGANISM: Artificial
<220> FEATURE:
<223> OTHER INFORMATION: primer

<400> SEQUENCE: 71
cgcccttgcg gtaatcg                                                       17

<210> SEQ ID NO 72
<211> LENGTH: 24
<212> TYPE: DNA
<213> ORGANISM: Artificial
<220> FEATURE:
<223> OTHER INFORMATION: primer

<400> SEQUENCE: 72
tacctttgcc atgtttcaga aaca                                               24

<210> SEQ ID NO 73
<211> LENGTH: 23
<212> TYPE: DNA
<213> ORGANISM: Artificial
<220> FEATURE:
<223> OTHER INFORMATION: primer

<400> SEQUENCE: 73
aatcaggtgc gacaatctat cga                                                23

<210> SEQ ID NO 74
<211> LENGTH: 22
<212> TYPE: DNA
<213> ORGANISM: Artificial
<220> FEATURE:
<223> OTHER INFORMATION: primer

<400> SEQUENCE: 74
attgacgtta cccgcagaag aa                                              22

<210> SEQ ID NO 75
<211> LENGTH: 21
<212> TYPE: DNA
<213> ORGANISM: Artificial
<220> FEATURE:
<223> OTHER INFORMATION: primer

<400> SEQUENCE: 75
gcttgcaccc tccgtattac c                                               21

<210> SEQ ID NO 76
<211> LENGTH: 49
<212> TYPE: DNA
<213> ORGANISM: Artificial
<220> FEATURE:
<223> OTHER INFORMATION: transcriptional initiation region of Pm in pLB1

<400> SEQUENCE: 76
cctaggcttt atgcaactag tacaataata atggagtcat gaacatatg                 49

<210> SEQ ID NO 77
<211> LENGTH: 49
<212> TYPE: DNA
<213> ORGANISM: Artificial
<220> FEATURE:
<223> OTHER INFORMATION: transcriptional initiation region of Pm in
      pIB11

<400> SEQUENCE: 77
cttaggcttt atgcaacatg tacaataata atggagtcat gaacatatg                 49

<210> SEQ ID NO 78
<211> LENGTH: 73
<212> TYPE: DNA
<213> ORGANISM: Artificial
<220> FEATURE:
<223> OTHER INFORMATION: transcriptional initiation region of Pm in pKO1

<400> SEQUENCE: 78
caacatgtac aataataatg gagtcatgaa catatgttat ttctctttct taaaaatatt     60
taattaaata atg                                                        73

<210> SEQ ID NO 79
<211> LENGTH: 53
<212> TYPE: DNA
<213> ORGANISM: Artificial
<220> FEATURE:
<223> OTHER INFORMATION: transcriptional initiation region in Pm in
      pKO1luc/celB

<400> SEQUENCE: 79
caacatgtac aataataatg gagtcatgaa catatgtatt taattaaata atg            53

<210> SEQ ID NO 80

```
<211> LENGTH: 26
<212> TYPE: DNA
<213> ORGANISM: Artificial
<220> FEATURE:
<223> OTHER INFORMATION: primer

<400> SEQUENCE: 80
cagtaatttc gaggatccgc attgtc                                          26

<210> SEQ ID NO 81
<211> LENGTH: 19
<212> TYPE: DNA
<213> ORGANISM: Artificial
<220> FEATURE:
<223> OTHER INFORMATION: primer

<400> SEQUENCE: 81
aaggatccgc gcgcgacca                                                  19

<210> SEQ ID NO 82
<211> LENGTH: 20
<212> TYPE: DNA
<213> ORGANISM: Artificial
<220> FEATURE:
<223> OTHER INFORMATION: primer

<400> SEQUENCE: 82
ggatgtgctg caaggcgatt                                                 20

<210> SEQ ID NO 83
<211> LENGTH: 26
<212> TYPE: DNA
<213> ORGANISM: Artificial
<220> FEATURE:
<223> OTHER INFORMATION: primer

<400> SEQUENCE: 83
ctggtcgaca gttaccaatg cttaat                                          26

<210> SEQ ID NO 84
<211> LENGTH: 18
<212> TYPE: DNA
<213> ORGANISM: Artificial
<220> FEATURE:
<223> OTHER INFORMATION: primer

<400> SEQUENCE: 84
gtcctcttag ttaaatgg                                                   18

<210> SEQ ID NO 85
<211> LENGTH: 15
<212> TYPE: DNA
<213> ORGANISM: Artificial
<220> FEATURE:
<223> OTHER INFORMATION: primer

<400> SEQUENCE: 85
aggaatcgaa cctgc                                                      15

<210> SEQ ID NO 86
<211> LENGTH: 53
<212> TYPE: DNA
<213> ORGANISM: Artificial sequence
<220> FEATURE:
<223> OTHER INFORMATION: region of bla and tRNA-Arg5 gene fusion in
      pLB11blaArg5
```

```
<400> SEQUENCE: 86
taactgtcga ctctagagga tccgcatttt cgaatttggt cgcgcgcgga tcc            53
```

ENHANCED EXPRESSION METHOD

RELATED APPLICATION

This application is a 371 of PCT/GB2007/002951 filed Aug. 3, 2007.

The specification incorporates by reference the Sequence Listing filed herewith entitled "Revised-Sequence-Listing.txt" created Sep. 30, 2014 and having a size of 15,521 bytes.

The present invention concerns methods of producing a desired heterologous gene product which is expressed from a strong promoter or in a strong expression system and particularly improvements in such methods. In particular, the methods of the invention involve enhancing the expression of the product by enhancing transcription of the gene. This is achieved by expressing the gene with (or, more generally put, by using) an mRNA leader which comprises one or more mutations which enhance the transcription of the gene. More specifically, one or more mutations may be introduced into the region encoding the mRNA leader. Mutations which enhance transcription of the desired gene may be selected. More generally, therefore, the invention provides a method of identifying or obtaining mRNA leader mutants which enhance expression (and particularly which enhance transcription) of a desired heterologous gene (encoding a desired heterologous gene product), which method comprises introducing one or more mutations into a DNA region corresponding to an mRNA leader and selecting an mRNA leader mutant (e.g. one or more mutants) which enhance(s) transcription of said gene.

The mechanisms underlying gene expression have been extensively studied in many organisms due to their fundamental importance for the understanding of cell function and for application in biotechnology. It is particularly important to have an understanding of the mechanisms affecting expression in recombinant protein production, to establish which factors may affect the level of expression.

It is well known in the art that protein production occurs through two basic steps, namely transcription (to form mRNA from the DNA template) and translation (of the mRNA to form a protein). Transcription can be delineated into three phases—initiation, elongation and termination. Hence, initiation of transcription begins with the binding of RNA polymerase to the promoter and ends with the conversion of the DNA and enzyme into an elongation complex. In between these steps, the polymerase and promoter undergo a series of alterations that include promoter binding and activation and RNA chain initiation and promoter escape. Promoter binding has been extensively studied in both prokaryotes and eukaryotes, where the interactions between RNA polymerase with general transcription factors, promoter specific factors and DNA sequences of the recognition regions of promoters have been investigated. The promoter binding-activation phase leads to the formation of the open promoter complex which interacts with NTP substrates to initiate transcription. Short RNA transcripts can then usually form which can be elongated if the polymerase escapes the promoter and moves downstream.

Promoter escape is the last stage of transcription initiation where the RNA polymerase should leave the promoter region and advance to downstream regions. If the RNA polymerase has a poor ability to escape the promoter, then abortive transcripts may be produced. Hence, the initial transcribing complexes carry out repeated initiation and abortive release without promoter escape (Hsu, Biochimia et Biophysics Acta, 1577, 191-207, 2002). In vitro studies have shown that changes in the promoter recognition region (from −60 to −1) may affect the abortive rate, probability and size of abortive transcripts (Vo et al, Biochemistry, 42, 3798-3811, 2003).

Hence, changes in the promoter and its recognition region have been studied in the art. Particularly, since the promoter plays an important part in the control of transcription, mutations in the promoter region have been previously studied to determine their effect on gene expression. For example, mutations in the Pm promoter at the −10 region which lies upstream of the transcriptional start site may facilitate gene-independent enhancement or reduction of expression and/or improved regulatory control of recombinant gene expression (WO 00/68375).

Translation of mRNA into protein occurs by interaction of mRNA with a ribosome. At least three different types of interactions between the mRNA and ribosome are known to occur. The protein moiety of the 30S subunit has an affinity for RNA, enabling binding in a non-sequence specific manner. Secondly, the 3' end of 16S rRNA interacts with a short stretch of complementary nucleotides, known as the Shine-Dalgarno sequence, located upstream from most natural initiation codons in the 5' untranslated region. Finally, the anticodon of fMet-tRNA pairs with the initiation codon.

It is well known that in bacteria the efficiency of ribosome binding is primarily determined by the secondary structure of the mRNA in the translational initiation region (the mRNA leader or 5' untranslated region, UTR). Mutations which have been made to hairpin structures in this region have been shown to effect the expression by translation (de Smit and van Duin, J. Mol. Biol. 244, 144-150, 1994). Further, alterations to the Shine-Dalgarno sequence in the 5' untranslated region have also been suggested to affect translation (Kozak, Gene, 234, 187-208, 1999).

In Komarova et al. (Journal of Bacteriology, 187, 1344-1349, 2005), it was found that extending the Shine-Dalgarno sequence in the mRNA leader reduced translation, although this inhibitory effect could be counter-acted by introducing into the leader AU-rich sequences which serve as targets for ribosomal protein S1, upstream of the Shine-Dalgarno sequence. Coleman and Nakamura (J. Mol. Biol., 181, 139-143, 1985) reported that mutations upstream of the ribosome binding site may affect translational efficiency. Mutations were made at or upstream of the Shine-Dalgarno sequence which varied the stability of mRNA by alteration of its secondary structure or removal of a portion of the Shine-Dalgarno sequence.

Therefore, it is well known in the art that mutations which affect the secondary structure of the mRNA leader or the Shine-Dalgarno sequence may affect translation.

Accordingly, in the context of production systems for desired proteins (i.e. the expression of recombinant genes) the factor (at the transcriptional and translational control levels) primarily thought to be important or determinative in the level, or indeed manner, of expression achieved is the promoter, at the transcriptional level. At the translational level, the mRNA leader is known to have an effect on gene expression, but generally speaking this has not been reported to be utilised in the context of industrial protein production. Thus, the promoter sequence has previously been recognised to have an effect on gene expression and mutations of the Shine-Dalgarno sequence or which affect secondary structures in mRNA (which may have a negative influence on translation), were thought to affect translation. In the context of protein production systems, the promoter has been subject to manipulation in an effort to improve the protein expression attainable, for example by selecting a particular promoter (e.g. a strong promoter or a tightly regulated promoter) or by modifying the promoter sequence. Whilst the mRNA leader is recognised to affect translation, it is not generally believed to be a factor manipulated in the context of a protein production system, other than in the context of modifying an unfavourable Shine-Dalgarno sequence or undesirable secondary structures.

Surprisingly, the present inventors have now found that mutations to the region encoding the 5' untranslated region (mRNA leader) can enhance gene expression through an enhanced transcriptional effect (more particularly, mutations can be made to this region which result in an increase in the amount of transcript which may be obtained), whereas previously this region was thought to be important primarily for translational effects. The construction of DNA libraries containing randomly mutated regions encoding (or corresponding to) 5' untranslated regions in E. coli, has allowed the identification of mutants which strongly stimulate gene expression, where the stimulatory effect is caused at least in part by transcriptional enhancement. Such UTR mutants have been shown to enhance the expression of a number of genes and the effects are largely believed to be independent of the promoter used. This finding is of clear interest in the field of biotechnology and for the production of recombinant proteins, where the possibility of increasing production of such proteins by enhancing transcription using such UTR mutants is clearly of commercial or industrial interest. The present invention is thus predicated on the novel and unexpected finding of a new role for the UTR in determining the level of gene expression. It is thus surprisingly proposed that, in order to enhance the transcription (and hence expression) of a gene (more specifically a recombinant gene), the UTR be modified.

More surprisingly, it appears that the transcriptional enhancement attainable by using the UTR mutants of the present invention can be employed to enhance the expression of genes from expression systems which are already efficient i.e. which are already working well to express the gene and produce the protein at levels which are commercially or industrially useful or relevant or acceptable according to the standards of the art, e.g. strong expression systems or systems which use a strong promoter. Prior to the present invention, it would not have been thought practical or feasible, or indeed possible, to achieve such a significant enhancement of expression in such an already efficient or already strong system by mutating the UTR. In other words such already efficient or already strong systems would not have been thought to be candidates for trying to achieve an enhancement or improvement in expression. In particular, it would not have heretofore been thought possible to gain or achieve enhancement of expression of a desired gene through enhancing transcription by mutating the mRNA leader. Accordingly, such an enhancement has not previously been demonstrated or suggested in the art and is of great interest for use in the expression of recombinant proteins. Hence, the present invention can be used to maximise gene expression.

The invention is thus based on introducing one or more mutations into the DNA corresponding to an mRNA leader (a UTR) and selecting a mutant mRNA leader (UTR) which enhances expression, and particularly transcription (e.g. by increasing the amount of transcript), of a desired gene (i.e. the gene it is desired to express). The step of introducing the mutations may thus be seen as generating a library of mRNA leader mutants which are then screened to select a mutant (e.g. one or more mutants) which enhances expression (and particularly transcription) of the desired gene. As explained further below, the mRNA leader which is subject to mutation can be selected according to choice, and need not be the leader which is particular or native to the desired gene.

As reported below, the effects of the mRNA leader mutants can to some degree be gene-dependent and thus particular mutants may work better with particular genes. In order to allow the selection of particular mutants which are optimal for a particular gene, the inventors have further developed a screening system, based on antibiotic resistance as explained further below, to allow the identification of mRNA leader mutants which stimulate the expression of a desired gene. This is a gene-selective screening system (i.e. it can select the mutants in a gene-specific or gene-dependent manner, in other words it is specific-gene-selective i.e. selective for a specific-gene) and is a powerful tool for identifying mutants which stimulate expression. Thus, the new assay, or screening method may be used to identify mutants which result in enhanced or stimulated expression, in terms of enhanced or stimulated protein output. Once mutants have been identified which stimulate expression, they can be tested for their ability to stimulate or enhance transcription e.g. by assessing (e.g. measuring) transcript levels. Mutants which stimulate or enhance transcription may be selected.

In one aspect, the present invention accordingly provides a method of producing a desired heterologous gene product wherein said heterologous gene product (or more particularly a gene encoding said heterologous gene product) is expressed from a strong promoter, said method comprising expressing said gene using a mutant mRNA leader which comprises one or more mutations which enhance transcription of said gene.

More particularly, in this method, expression of the gene (i.e. the gene encoding the desired heterologous gene product, hence the desired heterologous gene) is enhanced.

The modified (or mutant) mRNA leader may be obtained by introducing one or more mutations into the DNA region corresponding to the mRNA leader and selecting a mutant which enhances expression, and particularly transcription, of the desired gene.

Alternatively viewed, the invention provides a method of enhancing expression of a desired heterologous gene product wherein said heterologous gene product (or more particularly a gene encoding said heterologous gene product) is expressed from a strong promoter, said method comprising expressing said desired heterologous gene using a mutant mRNA leader which comprises one or more mutations which enhance transcription of said gene.

Said mutant mRNA leader may be obtained by introducing one or more mutations into the DNA corresponding to the mRNA leader and selecting a mutant which enhances expression, and particularly transcription, of the desired gene.

Accordingly, this aspect of the invention also provides a method of enhancing expression of a desired heterologous gene product wherein said heterologous gene product (or more particularly a gene encoding said heterologous gene product) is expressed from a strong promoter, said method comprising:

introducing one or more mutations into the DNA corresponding to an mRNA leader;
selecting an mRNA leader mutant which enhances transcription of the said desired gene;
expressing said gene using said mRNA leader mutant.

As referred to herein, enhanced (gene) expression means a level of gene expression which is increased as compared to, or relative to, the level of gene expression without the mutated leader, and more particularly as compared to, or relative to the mRNA leader before the mutations are introduced, i.e. in the absence of the (introduced) mutations. Such a leader may be a native leader, or any mRNA leader into which the mutations are introduced. Such an "unmutated" mRNA leader which is used as the starting point for the mutations introduced according to the present invention is also referred to herein as the "wild-type" leader. Thus, in other words enhanced gene expression is gene expression which is increased when using a mutant leader, or put more specifically a mutant DNA region corresponding to the mRNA leader, as compared, or relative, to the corresponding wild-type or unmutated leader or DNA region corresponding thereto. Thus, the expression attainable with the expression system according to the present invention i.e. with the strong promoter and with the mutant leader may be compared with the expression obtained from the same expression system, but using the unmutated or "wild-type" leader rather than the mutant leader. Hence, a "wild type" or "unmutated" expression system uses the same gene, mRNA leader (more specifically DNA region corresponding to the mRNA leader) and promoter as the system where enhanced expression is seen (i.e. by introducing modifications according to the present invention), but the mRNA leader is not modified or mutated. The mRNA leader used in a "wild-type" or "unmutated" expression system is therefore the unmutated or wild-type, mRNA leader, i.e. the "starting" leader, where no manipulations have been carried out to enhance expression. The wild-type leader is the leader before modification (before mutation) i.e. the leader into which the mutations are introduced. It may be seen as the "source" or "origin" or "starting" leader or the leader which is the substrate or target for the mutations (more particularly, references herein to the leader include, or refer to, the DNA corresponding to the mRNA leader). As noted above, the "unmutated" leader which is subject to mutation according to the present invention may be a native leader (i.e. a leader which occurs in nature) or it may be a synthetic or artificial leader or a native leader which is modified. Thus, the "unmutated" or "wild-type" starting leader need not be a naturally occurring leader, but may itself be a leader which has been modified or mutated over the native form, i.e. is a derivative or variant of a naturally occurring leader (e.g. a sequence modified derivative or variant) but which does not contain the mutations according to the present invention (i.e. does not contain the transcription-enhancing mutations which are introduced). In particular, any modification or mutation which the "unmutated" ("wild-type") leader may contain relative to the native leader as it occurs in nature does not affect expression, and particularly transcription.

According to the invention, gene expression is enhanced at least in part by enhanced transcription. However, translational effects may play a role and gene expression may be enhanced at both the transcriptional and translational levels. Thus, there may be an enhancement of both gene transcription and translation. More specifically, one or more of the mutations introduced may cause or result in enhanced translation as well as, or independently of enhanced transcription. What is required is that at least one of the mutations introduced causes or results in enhanced transcription. Hence, there may be other mutations in the leader which enhance translation in addition to the transcription-enhancing mutation(s) and/or the mutation which enhances transcription may itself enhance translation indirectly, e.g. by an increased number of transcripts being produced and/or directly e.g. by also affecting ribosome binding, or otherwise enhancing the process of translation. Notwithstanding this, an important aspect of the present invention is the enhancement of transcription, and particularly an increase in the amount of transcript produced.

An enhancement of translation can either occur as a result of an enhancement of transcription or can be independent of transcription. Hence, an enhancement of translation which is independent of transcription could result from, for example, more efficient ribosome binding and the actual process of translation, rather than as a result of more transcripts being present due to enhanced transcription. Such an enhancement of translation which is independent of transcription could be due to an alteration of the secondary structure of the mRNA leader sequence as reported in the art. An enhancement of translation which is a result of enhanced transcription is therefore due to, for example the increased number of transcripts being available for translation. Gene expression in the present invention may be enhanced by an enhancement of transcription and an enhancement of translation which is a direct result of the enhancement of transcription. However, enhancement of gene expression by an enhancement of transcription and an enhancement of translation which is both independent of transcription and as a direct result of transcription is also encompassed. It is possible for example that the mutations introduced into the region encoding the mRNA leader allow enhanced transcription (and enhanced translation may occur as a result of this) and that other mutations introduced improve the secondary structure of the mRNA leader to provide enhanced (transcription independent) translation. Alternatively, it is possible that a mutation introduced into the region encoding the mRNA leader allows enhanced transcription (and enhanced translation which is a direct result of the enhanced transcription) and also enhanced translation which is independent of the transcriptional effect, e.g. by improved ribosome binding. It is preferred in this instance that enhanced translation which is independent of transcription is not due to an improved secondary structure.

At least 20%, 30%, 40%, 50%, 60%, 70%, 80%, 90% or 100% of the enhanced gene expression may be caused as a result of enhancement of transcription. Preferably, at least 20%, 30%, 40%, 50%, 60%, 70% or 80% of the enhanced gene expression may be as a result of enhanced transcription e.g. as a result of the production of an increased number of transcripts. Whilst it may be possible that significant or substantially all of the enhancement of gene expression may be due to enhancement of transcription, it is generally observed that enhancement of transcription may be combined with an enhancement of translation. Enhanced gene expression (i.e. enhanced protein gene product) production may be seen with a combination of both transcriptional and translational effects (i.e. mutation(s) which enhance both transcription and translation).

Alternatively viewed, no more than 90%, 80%, 70%, 60%, 50%, 40%, 30%, 20% or 10% of the enhanced gene expression is caused by an enhancement of translation which is independent of enhanced transcription. In some cases it may be possible that not more than 5%, 4%, 3%, 2%, 1% of the enhanced gene expression is caused by an enhancement of translation, but as noted above, generally both transcriptional and translational effects are observed.

Expression of the gene product can be enhanced by up to, for example, 30 fold or more when using a mutated region encoding the mRNA leader compared to an unmutated or wild type leader, but it will be appreciated that this may vary significantly, depending upon the precise system used, and what the starting point is, for example' starting from a system using a leader where only low levels of expression are obtained, a much higher enhancement in the amount of protein product obtained may be achievable. Thus, an increase of expression (for example determined by the amount of protein produced) of 40- or 50-fold or more may be attainable. In other systems or under other conditions the increase may be less. By way of example only, expression of the gene product may be enhanced by at least 50, 40, 30, 27, 25, 24, 23, 22, 21, 20, 17, 15, 13, 10, 8, 6, 4 or 2 fold in a system using a mutant mRNA leader compared to expression using the corresponding unmutated or wild-type mRNA leader. Alternatively viewed, the minimum level of enhancement which can be seen is 1.1 fold, wherein expression can be enhanced by at least 1.2, 1.3, 1.4, 1.5, 1.6, 1.7, 1.8 or 1.9 fold. Gene expression can be increased by at least 10, 20, 30, 40, 50, 60, 70, 80, 90, or 100%. Other levels include at least 200, 300, 400 or 500%. The level of enhanced expression of the gene product can be measured by any convenient method known in the art. For example, expression can be determined by measuring protein activity (i.e. the activity of the expressed protein) wherein the levels of protein activity obtained using the mutant mRNA leader as opposed to the wild type mRNA leader are increased or enhanced. Alternatively, the amount of protein produced can be measured to determine the level of enhanced expression, for example by Western blotting or other antibody detection systems, or indeed by any method of assessing or quantifying protein. Many such methods are known in the art.

In order to identify mRNA leader mutants which stimulate or enhance expression, the desired protein product can be expressed with a tag or as a fusion protein e.g. a his tag or other suitable detection means, which can allow the measurement of gene expression using one assay for all different protein products. Particularly preferred as a method of identifying expression-enhanced mutants is to express the protein from an operon system, where the desired gene is translationally coupled to a reporter gene. Particularly, a reporter gene is selected whose expression level correlates with the expression level of the desired gene. The levels of expression of the desired gene can therefore be assessed or an indirect indication of its expression level may be obtained by measuring the level of the reporter gene which has been used. Reporter gene expression can be determined by the activity of the reporter gene. For example, if GFP was used, levels of fluorescence obtained would correlate to the level of gene expression of the desired gene product. Attractive reporters to use are those whose activity or presence it is possible to quantify or assess (e.g. semi-quantitatively) efficiently or readily, particularly those which result in growth or growth inhibition or cell death, as such reporters can be readily assessed by determining cell (e.g. colony) growth or non-growth. Antibiotic resistance markers fall into this category, e.g. bla encoding β-lactamase. Bla is particularly attractive as resistance correlates well to expression level. Reporters based on activity of the gene product may also be used e.g. reporter genes encoding an enzyme which may produce or be involved in the production of a detectable product or in a detectable reaction. An example of such a reporter is the luc gene encoding luciferase. Such "activity-based" reporters however require individual clones to be assayed. Particularly preferred reporter genes which can be translationally coupled to the gene expressing the desired gene product are beta-lactamase (bla) and firefly luciferase (luc).

The methods of the invention are for the production of a heterologous gene product by the expression of the gene encoding the desired product (i.e. by the expression of a heterologous gene). The present invention is thus concerned with methods of recombinant gene expression. As noted above, methods of recombinant gene expression are well known in the art and have been used industrially or commercially for the production of proteins. A variety of different expression systems are known and may be used to express the gene according to the present invention i.e. as the basis for the present invention. At its most basic, an expression system includes a promoter for expression of the desired gene and the gene it is desired to express, or a site for insertion of the desired gene, such that it may be expressed under the control of the promoter. According to the present invention, the expression system also includes an mRNA leader, or more precisely a DNA region corresponding to the leader. Also included may be other trancriptional or translational control elements necessary or desirable to achieve or optimize expression, as discussed further below.

Accordingly, the expression system which is used to produce the desired gene product whose expression is enhanced can be any system from which a gene can be expressed i.e. any system for the expression of a gene, more precisely for the expression of a recombinant gene. The expression system may be an in vivo or in vitro system and may for example be a vector e.g. a plasmid (including e.g. phagemids or cosmids) or an artificial chromosome or a viral vector, or a construct (e.g. expression casette) for insertion into a vector. The vector may be autonomously replicating or for chromosomal integration (e.g. a transposon-based vector or with sites for specific or homologous recombination for integration into the chromosome of the host cell into which the vector is introduced). The expression system according to the invention accordingly comprises a strong promoter, a region corresponding to an mRNA leader and a gene which encodes the desired gene product.

A vector may be introduced into a host cell, and the host cell may be grown or cultured to allow said gene to be expressed, e.g. under conditions which allow the gene to be expressed. Such expression methods are well known in the art and widely described in the literature. The host cell may be any convenient or desired host cell, and may be prokaryotic or eukaryotic. Thus, all types of prokaryotic cells are included, most notably bacteria, and eukaryotic cells may include yeast or mammalian cells. Prokaryotic expression systems are however preferred and particularly bacterial expression systems. Accordingly the desired gene is preferably expressed in a bacterial host cell.

The desired gene product is heterologous. In other words, a heterologous gene is expressed. The gene/gene product may be heterologous to the host cell used for expression. It may also be heterologous to the promoter and/or mRNA leader used i.e. to the expression system. Thus, the desired gene need not be used with its native promoter or mRNA leader. Indeed, it is usual to design an expression system with a promoter which is not native to the gene it is desired to express, i.e. containing a particular promoter for expression and in general the promoter will not be native to the gene it is desired to express. In recombinant expression, a gene may be expressed with its native mRNA leader, although more usually an expression vector is designed to include a sequence encoding a leader for expression of the gene. According to the present invention, the mRNA leader need not be the native leader of the gene. Thus, any mRNA leader may be used, or put more particularly, any DNA region corresponding to an mRNA leader. Thus, the region corresponding to the mRNA leader may be from, or may be derived from, any gene or any-gene system (e.g. operon etc). It may be, or may be derived from, the leader which is native to the gene to be expressed, or it may be heterelogous to the gene. It may, for example be, or may be derived from, the leader (more precisely the leader-corresponding sequence) which occurs naturally with the promoter which is used for expression i.e. which is native to the promoter. It may alternatively be non-native (heterologous) to both the promoter and the gene. As noted above, the mRNA leader may be used in its native form i.e. as it occurs in nature, or it may be modified or synthetic i.e. the "starting"

("unmutated") leader may be an mRNA leader which is modified over its native form. Accordingly, the promoter and mRNA leader-corresponding sequences which are used and into which mutations are introduced may not be those found naturally with the desired gene. Alternatively viewed, one or more of the promoter, region corresponding to the mRNA leader and gene may not occur naturally together. Hence, for example, preferably, the promoter and mRNA leader may be or may be derived from a promoter and mRNA leader which occur naturally together and not with the desired gene i.e. the gene is heterologous, or alternatively, the mRNA leader and gene are "native" to each other and not the promoter.

A preferred mRNA leader for use according to the present invention is or is based on that associated with the Pm promoter. Thus, the "Pm" leader is preferred to be used as the leader to be mutated according to the present invention and as used herein the term "Pm mRNA leader" includes not only the native Pm mRNA leader as it occurs in nature, but also derivatives or variants thereof, e.g. Pm mRNA leader sequences which have been modified over the native "original" sequence. The original Pm mRNA leader is described in Inouye et al (Gene, 29, 323-330, 1984). Pm mRNA leader derivatives or modified Pm mRNA leader sequences are described in Winther-Larsen et al (Metabolic Engineering, 2, 92-103, 2000).

Other representative mRNA leaders include the lac leader or derivatives thereof. The leaders from the promoters P7φ10 and Ptrc and derivatives thereof can also be used.

An expression system may contain any further elements necessary or desirable for expression e.g. enhancer sequences. Regulatory features may also be present e.g. start or stop codons, transcriptional initiators or terminators, ribosomal binding sites etc.

Further, selectable markers are also useful to include in the expression systems or vectors to facilitate the selection of transformants. A wide range of selectable markers are known in the art and are described in the literature. For example, antibiotic resistance markers can be used or the TOL plasmid Xyl E structural gene can be used. This encodes the product C230 which may readily be detected qualitatively or assayed. Spraying a plate of bacterial colonies with catechol rapidly distinguishes C230$^+$ colonies since they turn yellow due to the accumulation of 2-hydroxy muconic semialdehyde, enabling transformants/transconjugants etc rapidly to be identified by the presence of xylE in the vectors.

As mentioned previously, the expression system may also comprise a reporter gene or tag, e.g. which may be translationally coupled to the gene of interest. Representative reporter genes include any antibiotic resistance gene e.g. bla, or any gene encoding a detectable product or an enzyme which catalyses a detectable reaction e.g. lue.

The expression system may conveniently be in the form of a vector, as mentioned above. As noted above, a range of vectors are possible and any convenient or desired vector may be used e.g. a plasmid vector or a viral vector. A vast range of vectors and expression systems are known in the art and described in the literature and any of these may be used or modified for use according to the present invention. In a representative embodiment, vectors may be used which are based on the broad-host-range RK2 replicon, into which an appropriate strong promoter may be introduced. For example WO 98/08958 describes RK2-based plasmid vectors into which the Pm/xylS promoter system from a TOL plasmid has been introduced. Such vectors represent preferred vectors which may be used according to the present invention. Alternatively, any vector containing the Pm promoter may be used, whether in plasmid or any other form, e.g. a vector for chromosomal integration, for example a transposon-based vector. As noted above, the mRNA leader may preferably be or may be derived from the leader of the Pm promoter and accordingly, in one representative embodiment, the Pm promoter is used with a Pm mRNA leader.

Other vectors or expression systems which may be used include those based on or including the following promoters: Ptac, PtrcT7 RNA polymerase promoter ($P_7\phi10$), $\lambda P_L$ and $P_{BAD}$. The vectors may, as noted above, be in autonomously replicating form, typically plasmids, or may be designed for chromosomal integration. This may depend on the host organism used, for example in the case of host cells of Bacillus sp. chromosomal integration systems are used indusrially, but are less widely used in other prokaryotes. Generally speaking for chromosomal integration, transposon delivery vectors for suicide vectors may be used to achieve homologous recombination. In bacteria, plasmids are generally most widely used for protein production.

As noted above, any prokaryotic or eukaryotic cell may be used for expression, but preferably, a prokaryotic cell. This includes both Gram negative and Gram positive bacteria. Suitable bacteria include Escherichia sp., Salmonella, Klebsiella, Proteus, Yersinia, Azotobacter sp., Pseudomonas sp., Xanthomonas sp., Agrobacterium sp., Alcaligenes sp., Bordatella sp., Haemophilus influenzae, Methylophilus methylotrophus, Rhizobium sp., Thiobacillus sp. and Clavibacter sp. In a particularly preferred embodiment, expression of the desired gene product occurs in E. coli. Eukaryotic host cells may include yeast cells or mammalian cell lines.

The desired gene product may be encoded by any desired or cloned gene, including partial gene sequences, or any nucleotide sequence encoding a desired expression product, including fusion protein products. Hence the term "gene" refers to any nucleotide sequence which it is desired to express.

The gene product may be any protein it is desired to produce. The term "protein" is used broadly herein to include any protein, polypeptide or peptide sequence. This may for example be a commercially or industrially important protein. Desired gene products may thus include therapeutically active proteins, enzymes or any protein having a useful activity e.g. structural or binding proteins. Representative proteins may thus include enzymes involved in biosynthetic pathways or which make or are involved in the production of any useful product. Since the present invention is concerned with improving the production of commercially or industrially useful proteins, reporter genes or reporter gene products are not generally included as desired genes or desired gene products.

As used herein, the term "mRNA leader" or mRNA leader sequence is equivalent to the term "5' untranslated region" or "UTR" and refers to the transcribed mRNA sequence between the transcription start site and translation start site in mRNA. The mRNA leader sequence hence is the transcribed sequence which begins at position +1 which relates to the transcription start site and continues until the translation start site. The region corresponding to the mRNA leader (sequence) occurs at the DNA level rather than the RNA level and may therefore also be viewed as the DNA (e.g. DNA sequence or region) which encodes the leader. The region corresponding to the mRNA leader may thus also be seen as the DNA which is the complement of the mRNA leader or which templates its synthesis. This is also known as the initial transcribed sequence (ITS) at the DNA level. Mutation of the region encoding the mRNA leader sequence can alter the transcription start site by two to three base pairs—in such a situation, +1 will relate to the 'new' transcription start site and hence the mRNA leader sequence in this case will again be defined as the sequence between +1 which relates to the transcription start site and the translation start site in mRNA.

The initial transcribed sequence (ITS) occurs at the DNA level as noted above and corresponds to or encodes the transcribed mRNA leader sequence. Hence, reference herein to introducing one or more mutations into the mRNA leader, refers to the mutation of the corresponding DNA sequence, i.e. the ITS sequence. Mutation of this region produces corresponding mutations in the mRNA leader sequence which is the transcribed ITS.

The mRNA leader sequence or its corresponding ITS can typically be from 10 to 40 bases long, although it may be longer (e.g. up to 50, 60, 70, 80 or 100 or more bases). For example, the mRNA leader or ITS may be 30 bases long, or 25, 26, 27, 28 or 29 bases long, but this will of course depend on the gene or promoter from which the mRNA is obtained or derived. As described above, any region encoding an mRNA leader sequence can be used in combination with any gene to be expressed and any appropriate strong promoter. Preferably however, the mRNA leader used is native to either the promoter or the desired gene or is derived from such a native leader. As noted above a Pm mRNA leader sequence is preferred.

As used herein, the term "a strong promoter" refers to any strong promoter, which allows the gene under its control to be expressed at a high level. The strong promoter may be naturally occurring, or it may be a modified promoter or synthetic e.g. a derivative of a naturally occurring promoter. It may thus be native or non-native. The term "strong promoter" is a well-known term in the art and strong promoters are widely described in the literature. Hence, such a promoter can produce large amounts of transcript and final protein product from the gene of interest. For example, strong promoters can express proteins at a level of at least 1% of the total cellular protein. Preferably, a strong promoter can express proteins at a level of 2, 5, 10, 15, 20, 25, 30, 35, 40, 45 or 50% of the total cellular protein. In the context of a secreted or exported protein (e.g. an extracellular protein or one supplied with a secretory sequence) levels of 1% or more, or more particularly of 2% or more, of total cellular protein may be viewed as high, and accordingly indicative of a strong promoter. For an intracellular protein, levels of 5% or 7% or more, more particularly 10% or more, may be viewed as indicative of a strong promoter. This may depend upon the expression system, host cell and conditions used etc. Accordingly, a promoter may be a strong promoter if it achieves the above expression levels at the selected conditions in the context of a particular host cell and expression system i.e. it may be a strong promoter for the particular method and reagents used. Examples of strong promoters are well known in the art and any such promoters can be used in the expression system from which gene expression is enhanced. Such promoters for example include Pm promoter, Ptac, PtrcT7 RNA polymerase promoter ($P_7\phi10$), $\lambda P_L$ and $P_{BAD}$ or a derivative of any aforesaid promoter. Weak promoters are not included within the definition of strong promoters for the present invention and hence promoters such as $P_{CON}$ (Dobrynin et al., Nucleic acid Res. Symp. Ser., 7, 365-376, 1980) are excluded.

The promoter sequence can be found upstream of the transcription start site and is generally viewed as covering positions for example from −60 to −1, although this may vary. The promoter sequence hence does not include any of the transcribed sequence or the sequence at the DNA level which will be transcribed. The promoter Sequence does not therefore cover any of the sequence downstream of and including +1.

The present invention is particularly useful in providing a means for improving protein production processes, particularly commercial or industrial protein production processes. Thus, the present invention can be used to improve, or bring up to a satisfactory or commercially-acceptable level; expression processes which are operating (i.e. expressing the protein) at a level which is not high enough for industrial purposes. However; as noted above, the invention may also be used to improve further processes or expression systems which are already working efficiently e.g. where the levels of protein produced are acceptable at an industrial or commercial level.

Accordingly, alternatively viewed, the invention provides a method of producing a desired heterologous gene product wherein said heterologous gene product is produced by expression of a gene and the expression of said gene is enhanced from an already efficient expression system, said method comprising expressing said gene using a mutant mRNA leader which comprises one or more mutations which enhance transcription of said gene.

More particularly, in this method expression of the gene (i.e. the gene encoding the desired heterologous gene product, hence the desired heterologous gene) is enhanced.

The modified (or mutant) mRNA leader may be obtained by introducing one or more mutations into the DNA region corresponding to the mRNA leader and selecting a mutant which enhances expression, and particularly transcription, of the desired gene.

Also alternatively viewed, the invention provides a method of enhancing expression of a desired heterologous gene product wherein the expression of said gene is enhanced in an already efficient expression system, said method comprising expressing said gene using a mutant mRNA leader which comprises one or more mutations which enhance transcription of said gene.

Said mutant mRNA leader may be obtained by introducing one or more mutations into the DNA corresponding to the mRNA leader and selecting a mutant which enhances expression, and particularly transcription, of the desired gene.

Accordingly, this aspect of the invention also provides a method of enhancing expression of a desired heterologous gene product wherein the expression of said gene is enhanced in an already efficient expression system, said method comprising:

introducing one or more mutations into the DNA corresponding to an mRNA leader;

selecting an mRNA leader mutant which enhances transcription of the said desired gene;

expressing said gene using a said mRNA leader mutant.

In such alternatively viewed embodiments, an already efficient gene expression system may be seen as one which can express proteins at a level of at least 1% of the total cellular protein. Preferably, an already efficient expression system can express proteins at a level of 2, 5, 10, 15, 20, 25, 30, 35, 40, 45 or 50% of the total cellular protein. More particularly, for an exported or secreted protein the level may be 1% or more particularly 2% or more of total cellular protein and for an intracellular protein it may be 5% or more, or more particularly 7 or 10% or more. The considerations in relation to conditions and systems used, as mentioned above in the context of strong promoters, apply here also.

"Enhanced transcription" refers to an increase in the amount of transcript which may be obtained using a mutant mRNA leader according to the invention as compared to or relative to the level of transcription in the absence of the mutant leader and more particularly as compared with the corresponding unmutated leader i.e. the wild-type leader (see the definition of wild-type leader above). Enhanced transcription may be determined analogously to enhanced expression as set out above. Enhanced transcription is thus increased or stimulated transcription, or more particularly an increased or stimulated transcriptional effect, and results in an increase in the level or amount of transcripts obtained.

Enhanced transcription may result from an increase in the production of transcripts, or alternatively put an increase in the level of transcription, or from increased transcript stability or both. Different mutations introduced may contribute different effects. Some mutations in the mRNA leader allow increased transcription mainly by an increased transcriptional activity (i.e. increased transcript production) and mRNA stability in these mutants may play only a minor role. For example 10, 20, 30, 40, 50, 60, 70, 80 or 90% of enhanced transcription may be from an increase in transcript production (i.e. an increase in the level or amount of transcripts produced).

Generally, mutants are preferred according to the present invention in which there is at least some increase in transcript production (i.e. preferred mutants exhibit an increase in transcript production).

Preferably, transcription (i.e. the level or amount of transcript) can be enhanced by up to 30 fold or more compared to the unmutated leader. More preferably, transcription is enhanced by at least 25, 24, 23, 22, 21, 20, 17, 15, 13, 10, 8, 6, 4 or 2 fold compared to a wild-type or unmutated promoter. Alternatively viewed, the minimum increase in transcription (level or amount of transcript) which can be obtained is 1.1 fold, wherein transcription can be enhanced by at least 1.2, 1.3, 1.4, 1.5, 1.6, 1.7, 1.8 or 1.9 fold. Hence, the level of transcription when using the mutant leader is enhanced by at least 10, 20, 30, 40, 50, 60, 70, 80, 90 or 100%. Transcription can also be enhanced by 200, 300, 400 or 500%. The transcript level can be determined using any convenient method known in the art, for example by Northern blotting or array technology or real-time PCR. To assess transcript stability, mRNA decay may be measured, for example as described in the Example below.

An enhancement of translation refers to an increase in the amount of protein product obtained using a mutant leader as compared to or relative to the level of translation in the absence of the mutant leader, and more particularly as compared to the amount of protein product obtained using the unmutated leader. As mentioned previously, an enhancement of translation can be due to an enhancement of transcription which results in an increased level of transcripts being available for translation or can be independent of transcription and be due to for example enhanced ribosome binding to the transcripts. In the present invention, it is preferred that any enhancement of translation be due at least partly to an enhancement of transcription. For example, at least 10%, 20%, 30%, 40%, 50%, 60%, 70%, 80%, 90% or 100% of the enhancement of translation may be due to an enhancement of transcription.

Alternatively viewed, it is possible that no more than 50%, 40%, 30%, 20%, 10%, 5%, 2% or 1% of the enhancement of translation may be due to enhancement of translation which is independent of the enhancement of transcription.

An enhancement of translation refers to an enhancement of up to 50 fold or more compared to a wildtype leader. More preferably, translation can be enhanced by at least 40, 35, 30, 25, 24, 23, 22, 21, 20, 17, 15, 13, 10, 8, 6, 4 or 2 fold compared to translation from a wildtype leader.

Alternatively viewed, the minimum level of translation which can be obtained is 1.1 fold, wherein translation can be enhanced by at least 1.2, 1.3, 1.4, 1.5, 1.6, 1.7, 1.8 or 1.9 fold.

The level of enhancement of translation can be determined by measuring levels of protein expressed from the gene of interest or by measuring the activity of the desired gene product. Examples of such methods are discussed supra with regard to determining enhanced gene expression.

Mutations can be made to the region which corresponds to the mRNA leader (i.e. to the ITS) at any one or more positions from the transcription start site to the translation start site. A mutation can consist of an addition or deletion or substitution of any one or more nucleotides in the ITS which results in the addition or deletion or substitution of any one or more nucleotides in the mRNA leader. Addition or deletion mutations may involve the addition or deletion of one or more base pairs. Hence, 1, 2, 3, 4, 5, 6 or 7 or more bases can be inserted or deleted. In a particularly preferred embodiment, however, a mutation may be a substitution, which can occur at any position and may involve repetition (e.g. duplication) or inversion of fragments or segments of sequence. Hence, any of A, T(U), C or G can be substituted with a different base selected from A, T(U), C or G.

One or more mutations may be introduced to the ITS or mRNA leader. The one or mutations may be a combination of substitution, addition and/or deletion mutations or a number e.g. 2 or more additions or substitutions or deletions. Hence, a leader or ITS can contain for example both substitution and deletion mutations. Further, a leader or ITS may contain more than one substitution mutation at different positions in the leader. The length of the leader may also be increased, for example by introducing insertions or adding bases to one or both ends of the encoding sequence.

The number of mutations made is preferably in the range of 1 to 6, e.g. 2, 3, 4 or 5. For example, a mRNA leader or ITS may comprise 1, 2, 3, 4 or 5 substitution mutations, or may comprise 1 substitution mutation and 1 or more (e.g. 2 or 3) deletion mutations. Alternatively, substitution and/or deletion mutations may be coupled with mutations which extend the length of the leader.

The one or more mutations can be introduced into the ITS from position +1 i.e. the transcription start site or further downstream of this position. In a preferred embodiment, mutations are not present at the transcription start site or near to it, for example not within positions +1 to +7. Hence, mutation(s) may be present at position +8 or downstream therefrom, for example from +8 to +30, more particularly at any one or more of positions +8, +9, +10, +11, +12, +13, +14, +15, +16, +17, +18, +19, +20, +21, +22, +23, +24, +25, +26 and/or +27. In the case of a longer or extended leader, mutations may be introduced at downstream positions up to the length of the leader, i.e. at any one of positions +8 up to the translational start site (from +8 to the end of the ITS). As previously described, any mutation i.e. an addition, deletion or substitution can be made at any of these positions. Mutations can be introduced further downstream than position +20. For example at any one or more of residues +21, +22, +23, +24, +25, +26, +27, +28, +29 or +30 or further downstream, in the case of a longer leader. Thus, mutations can be introduced up to the translational start site at the end of the ITS.

Any such mutations may be generated by any method known in the art. For example, mutations may be made by mutagenesis which may be site directed or random. Random mutagenesis may be induced by chemically crosslinking agents or by radiation, for example exposure to UV light or may involve chemical modification of the nucleotides encoding or constituting the mRNA leader. Preferably mutations are introduced to the ITS sequence which corresponds to the mRNA leader at the DNA level. Further, the ITS can be mutated by using a 'doped' nucleotide mixture during its synthesis which corresponds to the mRNA leader, where at each step in polymerisation, the relevant wild type nucleotide is contaminated with the three other bases. This method enables the mutation frequency to be set at any particular level.

In a particularly preferred embodiment, the mutations introduced into the ITS or mRNA leader are non-predetermined mutations, or random mutations. Hence, the particular mutations which are introduced are not designed or specified before mutagenesis occurs. Thus, the mutations which occur are not predicted or determined. Any random mutagenesis method known in the art can be applied to produce the non-predetermined mutations e.g. radiation or using a 'doped' nucleotide mixture during mRNA leader synthesis as already described above. The introduction of non-predetermined mutations preferably refers to the initial screening stage of identifying mutations which enhance transcription and gene expression. Hence random mutagenesis is preferably used when identifying an enhancing mutation. However, once such a mutation has been identified then it can be introduced into a mRNA leader sequence by any mutagenesis method to provide the present invention. Therefore, in this way, a mutated mRNA leader can be selected which may be particularly suited to enhancing expression of a particular gene, e.g. in a preferred gene and promoter combination. However, mutated mRNA leaders which are found to enhance gene expression with one gene and/or promoter can also be used to enhance gene expression from a different gene and/or promoter. In other words, once a transcription-enhancing mRNA mutant has been identified it may be used with any gene, although it may be preferred to identity particular mutants for particular genes.

Further, in a preferred embodiment, the mutations introduced to the leader are not made to the Shine-Dalgarno sequence and/or do not establish or eliminate putative secondary structures. Further, the mutations do not include the insertion or creation of functional AU-rich sites, e.g. ribosomal protein binding sites (e.g. S1 binding sites) or enhancer elements. For example the insertion or creation of AU-rich tracts is not included e.g. AAGGAGGUGA (SEQ ID NO: 38), AAGGAGGU (SEQ ID NO: 39) or AAGGAG (SEQ ID NO: 40). The Shine-Dalgarno (SD) sequence is a short stretch of nucleotides located just upstream from most natural initiation codons with which the 3' end of 16S rRNA interacts. Usually, the Shine-Dalgarno sequence comprises GGAG (SEQ ID NO: 41) nucleotides or a similar sequence, e.g. AGGA (SEQ ID NO: 42). Excluded mutations to this sequence can hence consist of substitutions to the sequence and extending or reducing the length of the SD sequence. As mentioned above, the insertion or creation of AU-rich elements, for example sequences containing one or more repeats of AU, are preferably excluded from the present invention. The insertion of U-rich sequences into the mRNA leader are further preferably excluded as mutations made for the present invention. Further, in a preferred embodiment, the mutations made to the leader exclude the substitution of the entire leader sequence with a different leader sequence. Hence, in certain embodiments, at least 30%, 40%, 50%, 60%, 70%, 80%, 90%, 95%, 96%, 97%, 98% or 99% of the sequence of the wildtype mRNA leader is retained compared to the mutated sequence (note that the "wild-type" leader is the "unmutated" leader and hence need not be a naturally occurring leader—it may include other modifications or may be a synthetic or artificial leader).

Alternatively viewed, the mutated leader sequence has at least 30%, 40%, 50%, 60%, 70%, 80%, 90%, 95%, 96%, 97%, 98% or 99% identity to the wildtype mRNA leader sequence. Identity may be determined using the BestFit program of the Genetics Computer Group (GCG) Version 10 Software package from the University of Wisconsin. The program uses the local homology algorithm of Smith and Waterman with the default values. Gap creation penalty=8, Gap extension penalty=2, Average match=2.912, Average mismatch=2.003.

In another preferred embodiment, the one or more mutations which are introduced to the mRNA leader do not alter its secondary structure e.g. do not alter or change or create or eliminate hair pin loop or other secondary structures.

Hence in a most preferred embodiment, one or more non-predetermined substitution mutations are introduced to the mRNA leader sequence but not to the Shine-Dalgarno sequence.

Further, as discussed above, at least one of the mutation(s) introduced to the mRNA leader sequence enhances transcription, and particularly in certain embodiments increases transcript production. This mutation may also enhance translation and/or there may be other mutations in the mRNA leader sequence which enhance translation.

Although any mRNA leader can be mutated in the present invention, in a preferred embodiment the invention uses the mRNA leader sequence which occurs naturally with the Pm promoter (a "Pm mRNA leader") which includes derivatives of the native sequence. Hence, in one embodiment according to the present invention, one or more mutations may be made to the sequence aactagtacaataataatggagtcatgaacatatg (SEQ ID No. 1) which is the DNA sequence (or ITS) corresponding to a Pm leader. A representative mutant Pm mRNA leader may have a sequence selected from SEQ ID NOs. 2-12 and 14-37 as shown in Table 4. However, it will be understood that these mutants were identified by screening using particular genes. As explained above, the effects of the mutations may in some cases and/or to some degree be gene-specific or gene-dependent. Accordingly, whilst it may be the case that some mutants may be useful with different genes, particular mutants are not generally regarded to be of universal application, and mutants will be selected for particular genes.

In a further embodiment, the present invention therefore encompasses a Pm mRNA leader sequence which comprises one or more mutations as compared to the wildtype Pm mRNA leader sequence, wherein said mutant mRNA leader sequence is capable of enhancing expression (more particularly transcription) of a desired gene product.

Also included is the mutant DNA sequence (ITS) corresponding to the said mutant Pm leader.

The Pm mRNA leaders can be mutated at any one of positions +1 to +35 and as described previously such mutations can be selected from any one or more of a substitution mutation, a deletion mutation and an addition mutation. Preferably, positions +4 and +7 are not mutated.

Mutations are hence preferably found within the range of position +2 to position +27, more preferably within the range from position +2 to +18, for example mutations maybe found at one or more of +2, +3, +5, +6, +8, +9, +10, +11, +12, +13, +14, +15, +16 and +17.

Representative mutated Pm ITS or mRNA leaders encompassed by the invention are those of SEQ ID NOs 2-12 and 14-37.

Vectors comprising the mutant Pm ITS or mRNA leader sequences of the invention and cells and libraries comprising such vectors or the mutant Pm mRNA leader sequences are also encompassed.

The mutated leader, or more particularly ITS can be used to enhance expression of any gene product. However, in a preferred embodiment, the ITS can be mutated and specific mutants tailored for the enhanced expression of a particular gene may be selected. Hence, such mutants may be identified by using them in an expression system with the desired gene and the mutants giving the highest levels of enhanced expression may be selected. Such mutant ITS sequences may be selected and sequenced. These sequences, although specifically selected for enhanced expression of one gene can however still be used for the enhanced expression of other genes.

A further aspect of the present invention includes a method of obtaining a mRNA leader mutant capable of enhancing the transcription of a desired gene, said method comprising introducing one or more mutations into the DNA corresponding to an mRNA leader;

selecting an mRNA leader mutant which enhances transcription of the said desired gene.

More particularly, this aspect of the invention provides a method of obtaining a mRNA leader mutant capable of enhancing the transcription of a desired gene, said method comprising introducing one or more mutations into the DNA corresponding to an mRNA leader;

expressing said desired gene using said mRNA leader mutant in a host cell and selecting an mRNA leader mutant which enhances transcription of the said desired gene.

Preferably the gene is desired to be expressed using a strong promoter or in an already efficient expression system and/or is a heterologous gene.

The step of introducing the mutations can be seen to generate a library of mRNA leader mutants (more precisely ITS mutants or mutants of the region corresponding to the leader). This library may then be screened to select a mutant which enhances transcription of a desired gene.

The library may contain two or more mutants, preferably 3, 4, 5, 6, 8, 10, 12, 15, 18, 20, 22, 25, 30, 40, 50 or more mutants.

The method of this aspect of the invention may thus be seen as a method for screening or identifying or selecting mRNA leader mutants.

The one or more mutations can be introduced into the ITS by any method already described above, although in a most preferred embodiment, one or more mutations are introduced by using a "doped" nucleotide mixture at each step in the polymerisation of the synthesis of one strand of a synthetic oligonucleotide covering the mRNA leader.

As described above, the methods of screening can be used to select a mutant ITS which is tailored or selected for particularly high enhanced expression for a particular gene, although such mutants can in any case then be used to enhance expression of other gene products.

The selection of an mRNA leader or ITS mutant which can enhance expression of the desired gene product by enhancing transcription may be carried out using methods well known in the art. For example, the activity of the gene product can be measured, e.g. by ELISA or a similar assay, and the activity obtained using the mutant mRNA leader can be compared to that obtained using the wild type leader. Hence, a comparison of the activity levels obtained when using both the wildtype and mutant mRNA leader sequences will identify those mutants which have enhanced protein activity and hence gene expression. Once such enhanced expression mutants have been identified transcriptional effects can be investigated for example by determining transcript levels. Transcript levels may be measured or assessed as described above. Alternatively transcript levels may be directly assessed or determined to select the mutants. A mutant mRNA leader or ITS can be assessed for its ability to enhance gene expression by either investigating the levels of a reporter gene product which is produced (which can either be produced on its own, or as a fusion protein with the desired gene product, or more advantageously by translational coupling of reporter gene expression to the-expression of the desired gene), or by directly investigating the levels of desired gene product produced. Hence, in a preferred embodiment the selecting step may involve the assessment or determination of levels or the activity of a reporter gene. In a particularly preferred embodiment the reporter gene is an antibiotic resistance marker e.g. bla or encodes a detectable product, or a product which results in the production of a detectable product e.g. luc or celB. Therefore, mRNA mutant leaders which can enhance expression can be screened for example by detecting colonies of cells transformed with the expression system comprising the strong promoter, mutant mRNA leader and reporter gene, which can grow on media containing high concentrations of penicillin (when the reporter gene is bla) or other antibiotic. For example, a penicillin concentration in the range 1-15 mg/ml, may be used to select high expressers but this can be reduced by using a construct designed in a particular way, for example, having a mutation in the Shine-Dalgarno sequence to reduce translation. This would provide a wider window for identification of transcriptional stimulation, because addition of more than 15 mg/ml penicillin is impractical. Alternatively, the amount of gene product obtained with the mutant mRNA leader can be measured using for example Western blotting and compared to that obtained when using the wild-type unmutated leader. Those mutants having enhanced expression as defined herein are selected in accordance with the present invention. Such a method may not be practical for low frequency mutants.

To screen for mutant ITS or mRNA leader sequences which have enhanced transcription, methods such as Northern blotting and microarray technologies can be employed to select enhanced transcription levels.

In a further embodiment, the invention provides a method of obtaining an mRNA leader mutant which is capable of enhancing expression of a desired gene, said method comprising the steps of a) introducing one or more mutations into the mRNA leader sequence of interest, b) producing a library comprising the mutant mRNA leader sequences of interest upstream of the gene of interest or of a reporter gene, and c) screening the library for mRNA leader mutants which enhance expression of said desired gene or reporter gene. More particularly transcription is enhanced.

In this way, a library of mutated mRNA leader sequences can be screened, wherein, clones expressing protein at the required levels can be selected using methods described above e.g. Western blotting, or by using a reporter gene e.g. bla. By using the desired gene of interest in the method of screening, mutant ITS sequences which are tailored or optimum or selected for enhanced expression of that gene can be selected. If a reporter gene alone is used in the method of screening, then mutated ITS sequences which may have general application may be selected.

However, since the effects of the mutants can be gene-dependent, it is preferred to select the mutants with reference to the desired gene. Since it would be laborious to design and construct separate expression systems for every desired gene, the inventors have devised a system where the expression of the desired gene (i.e. the test or target gene) is coupled to the expression of a reporter gene. This may be achieved by translational coupling using the phenomenon of translational reinitiation (Adkin and Van Duin, 1990, J. Mol. Biol., 213, 811-818; André et al., 2000, Febs Letters, 468, 73-78). Thus, the desired (test) gene may be inserted into an expression vector downstream of a promoter and a reporter gene is inserted as a second gene in such a way that its translation is coupled to the translation of the upstream gene (the desired or test gene) through overlapping or closely positioned stop and start sites. Thus the level of expression of the desired gene determines the level of expression of the reporter gene. Reporter gene expression is thus an indicator of the level of desired gene expression, and may be determined to determine desired gene expression. Convenient reporter genes to use are antibiotic resistance genes for example bla or the kanamycin resistance gene. Any desired gene may thus be inserted into such a "screening vector" which may contain a mutant mRNA leader for selection. A library of mutants may be generated in such a "screening vector". Such coupled genes may constitute an artificial operon which may be used in the selection step.

Accordingly, in a preferred embodiment, an artificially constructed operon can be used to screen mutant ITS/mRNA leader sequences in a library or otherwise. Such an operon may be contained in any convenient vector, for example in a plasmid. Such an operon incorporates the desired gene whose expression is to be enhanced and a reporter gene, conveniently an antibiotic resistance marker gene e.g. bla (which encodes beta-lactamase and confers resistance to penicillin as previously described). The desired gene is positioned upstream of the reporter gene and the reporter gene is expressed by translational coupling with the desired gene. The vector further comprises the mutant mRNA leader sequence and promoter upstream of the gene of interest (ideally this will be the strong promoter from which it is desired to express the gene according to the methods above). Hence, the heterologous gene product is produced together with the reporter gene and in such a way, the expression of the reporter gene can be used to measure the expression of the desired gene.

The present invention accordingly provides a method of identifying (or screening for) an mRNA leader mutant which enhances expression of a desired gene, said method comprising:

providing a vector comprising a promoter, a said desired gene under the control of said promoter and a reporter gene translationally coupled thereto;

introducing a DNA sequence corresponding to said mRNA leader mutant into said vector upstream of said desired gene;

determining the level of expression of said reporter gene.

By determining the level of reporter gene expression, the level of desired gene expression may be determined.

Mutants which enhance expression of the desired gene may be determined by comparing the level of expression (i.e. reporter gene expression) with that obtained using the corresponding unmutated (i.e. wild-type) leader.

Thus to determine the level of expression, a said vector is introduced into a host cell, and said host cell is cultured or grown to allow said desired and reporter genes to be expressed (e.g. under conditions which allow said genes to be expressed).

The promoter is preferably a strong promoter.

The mutant mRNA leader library can be made in prokaryotic cells, preferably in *E. coli*. Other cell types can be used to create the library, examples of which have been described supra. Hence, mutant libraries can be created using for example the expression systems already described or the artificially constructed operon. Such a library is plated onto agar plates, where the number of transformants may be about 100000. Clones containing the artificially constructed operon can be selected for by antibiotic resistance, e.g. by resistance to ampicillin, where such a resistance gene is also present in the operon or vector containing the operon. Appropriate selectable markers have been discussed supra. High expression mutants can be screened for by detecting enhanced expression of the reporter gene or the desired gene product and can be sequenced to identify the mutation(s) responsible for enhanced expression.

Further encompassed by the present invention is an artificially constructed operon, or a vector, comprising the desired gene, translationally coupled to a reporter gene, wherein said desired gene and reporter gene are under the control of a promoter, preferably a strong promoter, and a mutant ITS or mRNA leader, as defined herein.

This aspect of the invention may provide a vector for selection or identification of an mRNA leader mutant as defined herein, said vector comprising a promoter, a desired (or test) gene under the control of said promoter and a reporter gene translationally coupled thereto, and a site for insertion of a DNA region corresponding to the said leader mutant upstream of said desired gene.

In a further aspect, the vector may comprise the DNA region corresponding to the said leader mutant upstream of said desired gene. Accordingly the invention also provides a library of such vectors. The vectors in the library may comprise different mRNA leader mutants.

The use of a such an operon or vector for screening of mutant ITS/mRNA leaders for leader sequences which result in enhanced expression of a desired gene is also encompassed.

As noted above, the methods of the invention find particular utility in the commercial or industrial production of proteins. In a preferred aspect, therefore the methods of producing a protein or of enhancing expression of a protein relate to production-scale processes i.e. they are carried out on a production-scale or industrial scale, rather than a laboratory experiment. The processes may be preferred in a bio-reactor or fermentor, particularly a production-scale bio-reactor or fermentor.

The invention will now be described in more detail in the following non-limiting Example with reference to the following drawings:

FIG. 1: Map of the plasmids pLB1 and pIB11. The restriction sites shown are unique. bla, gene encoding β-lactamase; Km$^r$, kanamycin resistance gene; trfA, gene encoding the essential replication protein; xylS, gene encoding the transcriptional activator XylS; oriV, origin of vegetative replication; oriT, origin of transfer; t, bidirectional transcriptional terminator. The difference in size between pIB11 and pLB1 is caused by the substitution of the original XbaI/MunI fragment in pJT19bla directly upstream of the Pm promoter, which is kept in pLB1, with a XbaI/MunI fragment containing rrnBT1T2 in pIB11. rrnBT1T2 is a transcriptional terminator. Details for the transcriptional and translational initiation regions of Pm in the two constructs are displayed above the plasmid map, where i) gives the details for pLB1 (SEQ ID NO: 76) and ii) shows the details for pIB11 (SEQ ID NO: 77). Nucleotides written in lowercase were randomly mutagenized by the use of a mixed oligonucleotide mixture. The transcriptional start site indicated for the pLB1 construct (i) is assumed to be the same as in the pJT19bla construct, which is the basis for the pLB1 construct (Winther-Larsen et al., 2000, Metab. Eng., 2, 92-103). The transcriptional start site indicated for the pIB11 construct (ii) is based on primer extension analysis results for the pIB6 construct only differing at one nucleotide in the SD-region (see Materials and Methods) (Bakke et al., 2006 manuscript in preparation).

Figure 2:
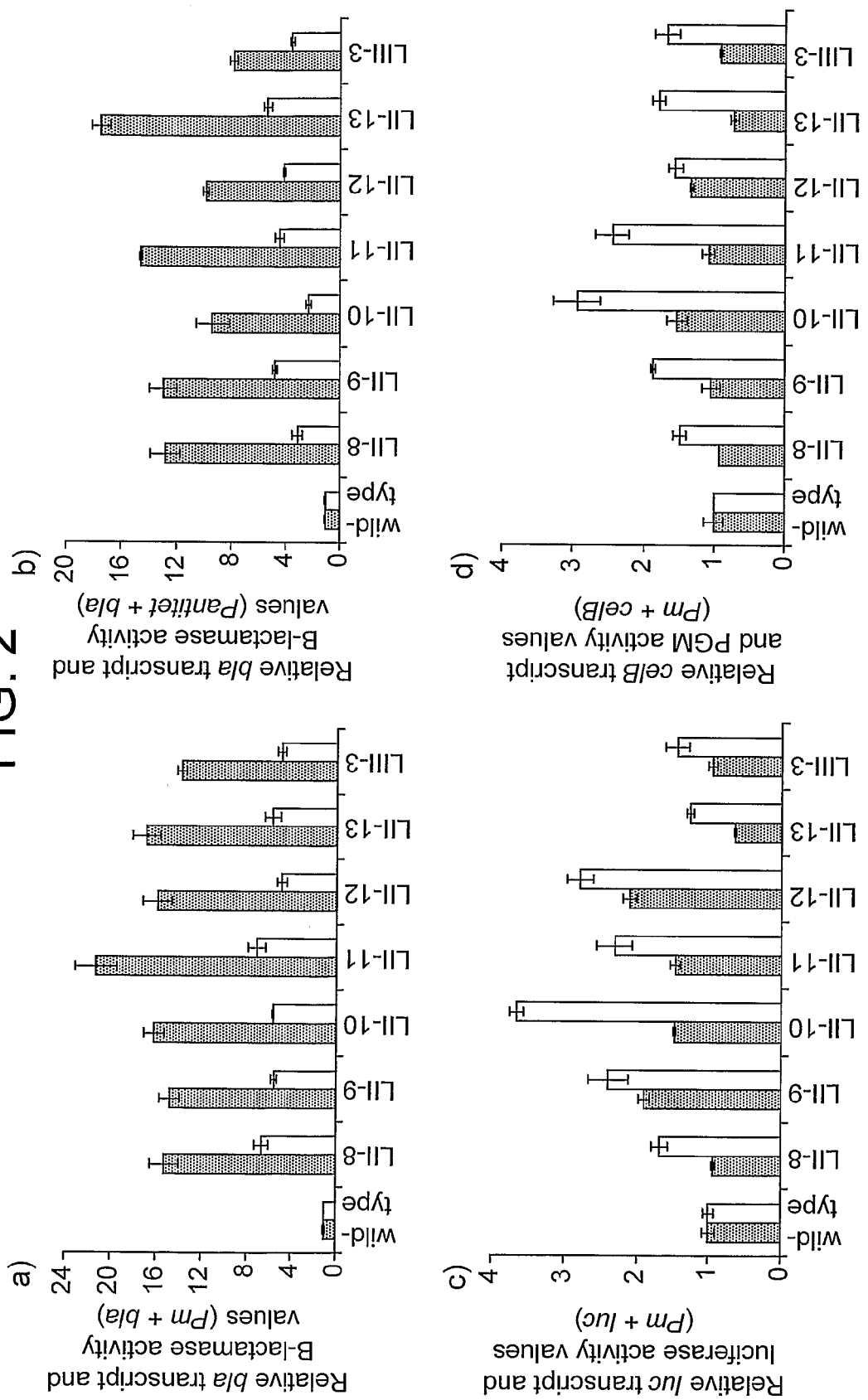

FIG. 2: Phenotypes of seven UTR high expression level mutants isolated from the LII and LIII libraries. Enzyme activities (grey) and transcript amounts (white), relative to the wild-type for a) Pm combined with bla (pIB11), b) $P_{anti-tet}$ combined with bla (pLB9), c) Pm combined with luc (pKT1) and d) Pm combined with celB (pLB11). The values are the average of at least two different experiments, and the bars show the deviation between the experiments. The wild-type values are arbitrarily set at 1. The cultures were grown at 37° C. to an optical density at 600 nm of 0.1, induced with 2 mM m-toluate and further grown for 5 hours at 30° C. The cultures were then harvested for Real-Time PCR analyses and enzyme activity assays.

Figure 3:
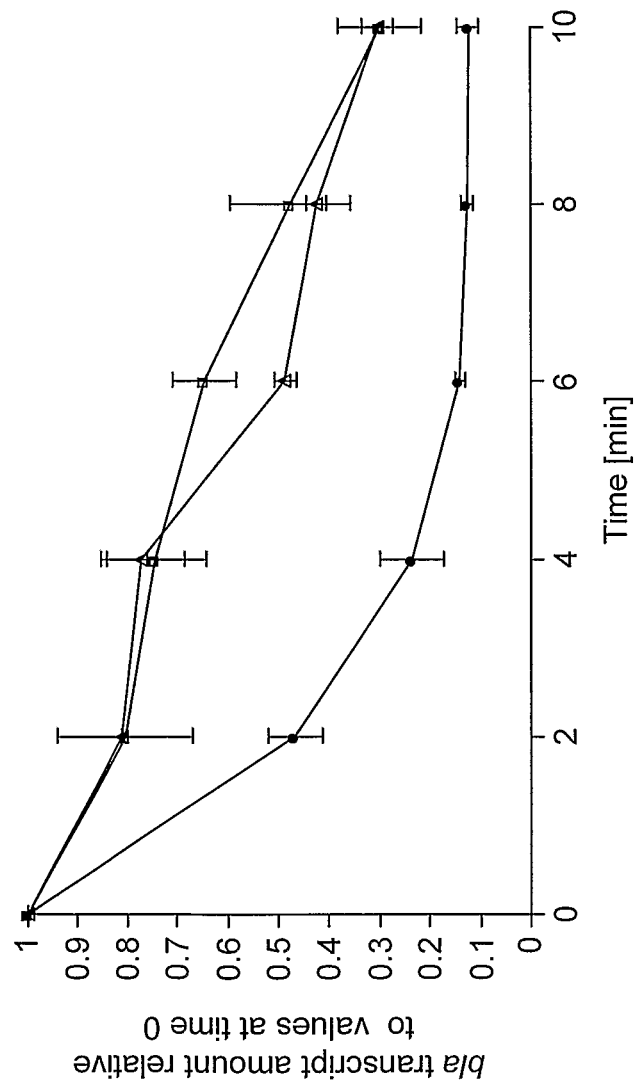

FIG. 3: Stability/decay of bla mRNA from the pLB9 ($P_{anti-tet}$+bla) wild type (dots) and high level expression UTR mutants LII-11 (squares) and LII-13 (triangles). Transcript amounts were measured by Real time PCR using SYBR green. The values are the average of at least two different experiments, and the bars show the deviation between the experiments. The cultures were grown at 30° C. for approximately 5 hours before addition of rifampicin to a concentration of 200 µg/mL at time 0.

Figure 4:
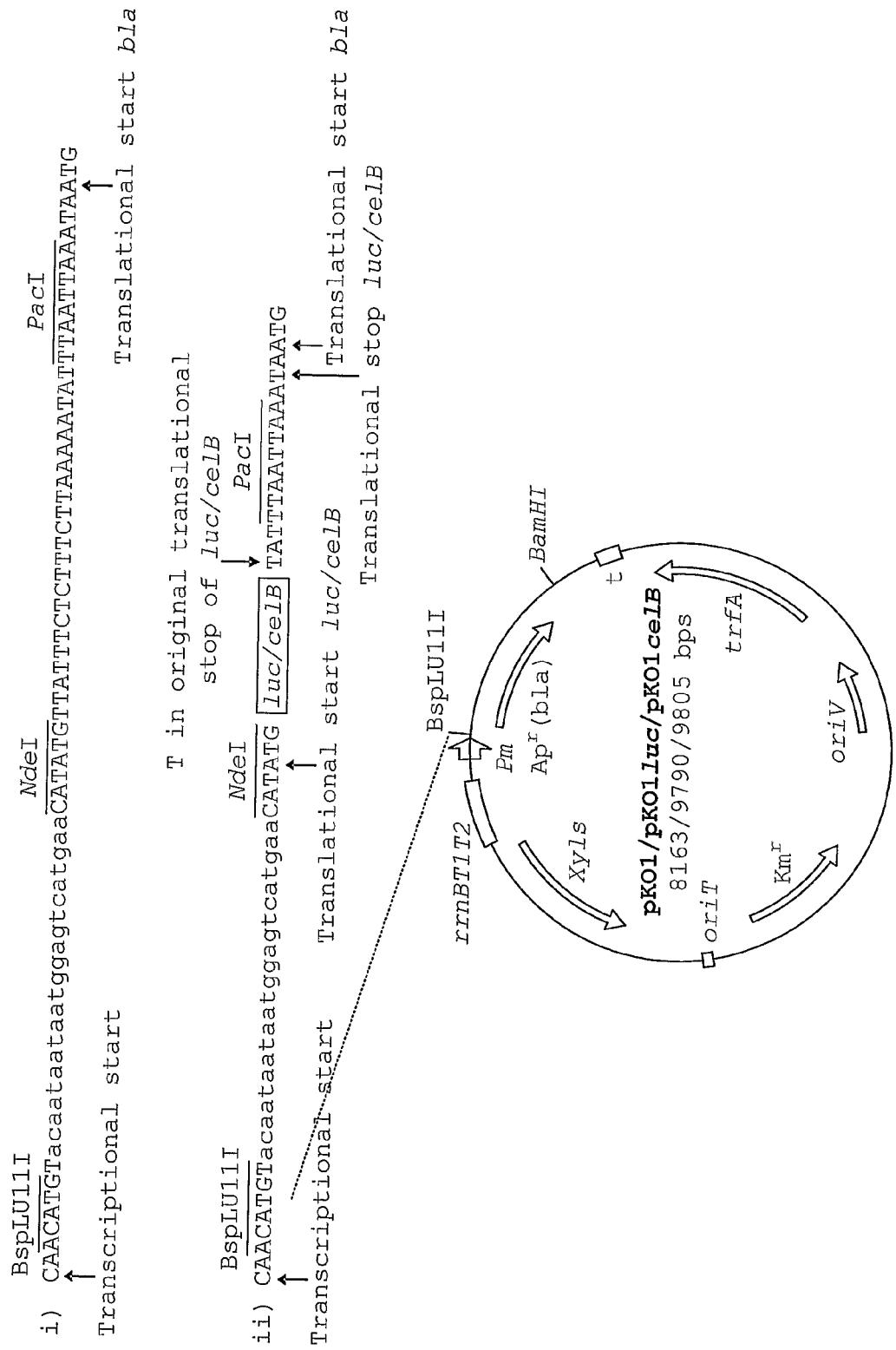

FIG. 4: Map of the synthetic operon constructs pKO1, pKO1luc and pKOcelB. The restriction sites shown are unique. bla, gene encoding β-lactamase; Km$^r$, kanamycin resistance gene; trfA, gene encoding the essential replication protein; xylS, gene encoding the activator XylS; oriV, origin of vegetative replication; oriT, origin of transfer; t, bidirectional transcriptional terminator; rrnBT1T2, transcriptional terminator. Details for the transcriptional and translational initiation regions of Pm in the two constructs are displayed above the plasmid map, where i) gives the details for pKO1 (SEQ ID NO: 78) and ii) shows the details for pKO1luc/celB (SEQ ID NO: 79). The constructs are made such that four amino acids are added at the C-termini of the Luc and CelB proteins. Nucleotides typed in lowercase were randomly mutagenized by the use of a mixed oligonucleotide solution. The transcriptional start site for the Pm promoter in the synthetic operon constructs is assumed to be identical to its start site in the pIB11 construct, of which the synthetic operon constructs are based. The pKO1 plasmid is constructed for easy insertion of any gene of interest in the same way as luc and celB.

Figure 5:
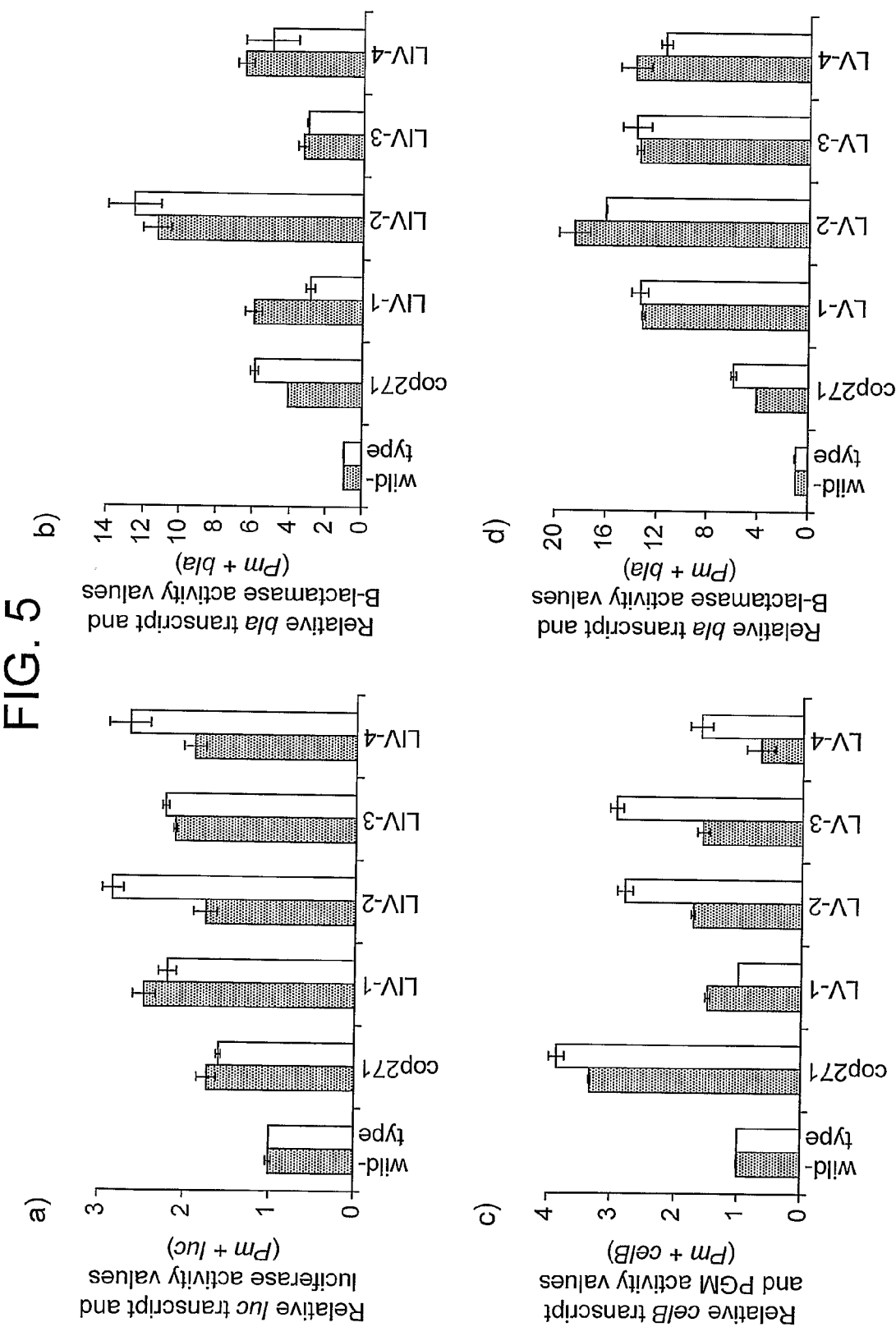

FIG. 5: Phenotypes of the isolated UTR high expression level mutants from the LIV (pKO1luc) and LV (pKO1celB) libraries. The phenotype of the plasmid copy-up mutant trfA cop271C inserted in the wild-type UTR constructs of pKT1, pIB11 and pLB11 are also included. Enzyme activities (gray) and transcript amounts (white) relative to the wild-type for: UTR high-level expression mutants, LIV-1 to -4 cloned into the pKT1 construct (Pm+luc) (a) and the pIB11 construct (Pm+bla) (b), and UTR high-level expression mutants, LV-1 to -4 cloned into the pLB11 construct (Pm+celB) (c) and the pIB11 construct (Pm+bla) (d). The values are the average of at least two different experiments, and the bars show the deviation between the experiments. The wild-type values were arbitrarily set to 1. The cultures were grown at 37° C. until an optical density at 600 mu of 0.1, induced with 2 mM m-toluate and further grown for 5 hours at 30° C. The cultures were hen harvested for Real-Time PCR analyses and enzyme activity assays.

Figure 6:
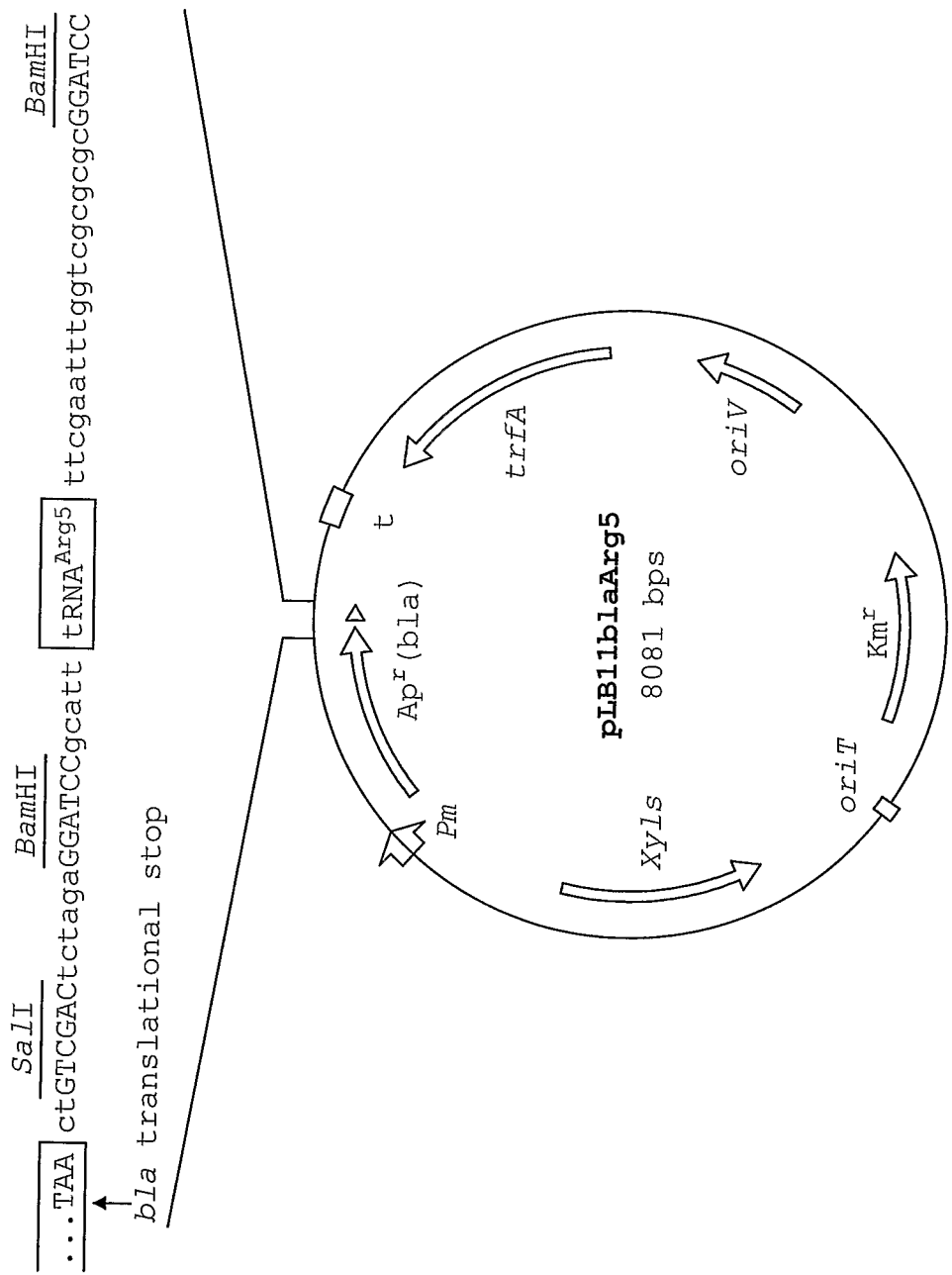

FIG. 6: Map of the plasmid pLB11blaArg5. The restriction sites shown are unique. bla, gene encoding β-lactamase; tRNA$^{Arg5}$, recognizes the rare arginine codon AGG; Km$^r$, kanamycin resistance gene; trfA, gene encoding the essential replication protein; xylS, gene encoding the activator XylS; oriV, origin of vegetative replication; oriT, origin of transfer; t, bidirectional transcriptional terminator. bla translational stop codon, and tRNA$^{Arg5}$ gene are depicted as outlined rectangular boxes in SEQ ID NO: 86. Triangles indicate the direction of transcription.

EXAMPLE 1

Materials and Methods
Bacterial Strains, Plasmids, and Growth Media

The bacterial strain and plasmids used in this study are described in Table 1. In all experiments, cells were grown in L broth (10 g/liter tryptone, 5 g/liter yeast extract, and 5 g/liter NaCl) or on L agar at 37° C., except for expression studies where 30° C. was used. Kanamycin (Km) was always used at a concentration of 50 µg/ml. Ampicillin was used in expression studies, and concentrations are reported with the results.
DNA Transformation In cloning experiments, transformations of E. coli were performed using a modified RbCl protocol (www.promega.com).
DNA Manipulations Plasmid DNA was prepared by the WizardPlus SV minipreps DNA purification kit (Promega) or the Qiagen Plasmid Midi Kit (Qiagen). Enzymatic manipulations were performed as described by the manufacturers. DNA was extracted from agarose gel slabs using the Qiaquick gel extraction kit (Qiagen) or the Qiaexll DNA extraction from agarose kit (Qiagen). PCR reactions were performed using the Expand High Fidelity PCR system kit (Boehringer Mannheim) for cloning purposes. Site-directed mutagenesis was performed using QuickChange Site-Directed Mutagenesis Kit (Stratagene). When PCR was used for generation of templates for DNA sequencing, the polymerase DynazymeII (Finnzymes) was used. PCR templates were treated with the enzyme mixture. ExoSapIt (USB) prior to DNA sequencing. Sequencing reactions were carried out using the ABI PRISM BigDye sequencing kit (Applied Biosystems), and analyzed using an ABI PRISM 3130×1 Genetic Analyzer sequencing machine (Applied Biosystems). The AvrII site upstream of the transcriptional start site of pLB1 was introduced by site specific mutagenesis of pTA8 using the QuickChange Site-Directed Mutagenesis Kit (Stratagene) as described by the manufacturers and the primers 5'-GAAAGGCCTACCCCCTAG-GCTTTATGCAACTAG-3'. (SEQ ID NO. 43) and 5'-CTAGTTGCATAAAGCCTAGGGGGTAGGCCTTTC-3' (SEQ ID NO. 44).

The wild type Pm 5' untranslated transcript region was introduced into pIB6 generating pIB11 by the cloning of two annealed, complementary oligonucleotides with the wild type Pm 5' untranslated transcript sequence and BspLU11I- and NdeI-compatible ends, for subsequent cloning into the pIB11 vector. Sequences of oligonucleotides were 5'-CATG-TACAATAATAATGGAGTCATGAACA-3' (SEQ ID NO. 45) and 5'-TATGTTCATGACTCCATTATTATTGTA-3' (SEQ ID No. 46). Cloning of the $P_{anti-tet}$ promoter from pBR322 into pIB11 to generate pLB9 was done by PCR amplification with the primers 5'-AGCCTATGCCTA-GATCTTCCAGGGTGACG-3' (SEQ ID NO. 47) and 5'-TATCATCGATAACATGTAATGCGGTAG-3' (SEQ ID NO. 48) which introduced the restriction sites for XbaI and BspLU11I, respectively, for cloning purposes.

Construction of the artifical operon construct, pKO1 (FIG. 4), was performed by PCR amplification of the pIB11 with the primers 5'TCATGAACATATGTTATTTCTCTTTCT-TAAAAATATTTAATTAAATAAT GAGTATTCAA-CATTTCCGTGT (SEQ ID NO. 49) and 5'-AGCTAGAG-GATCCCCGGGTA-3' (SEQ ID NO. 50). The first primer introduced a 37 bp addition between the NdeI restriction site and the second codon of bla containing the PacI restriction site and the translational overlapping stop and bla start codon downstream of the Pm 5' untranslated transcript. This fragment was cloned into the pIB11 vector using the NdeI and BamHI restriction sites (FIG. 1). The pKO1luc plasmid (FIG. 4) was constructed by PCR amplification of the luc gene from pKT1 using the primers 5'-TCATGAACATATGGAAGACGCCA-3' (SEQ ID NO. 51) and 5'-GCTGAATACATTAAT-TAAATACAATTTGGA-3' (SEQ ID NO. 52) which introduced the NdeI and PacI restriction sites, respectively, for cloning purposes. Also, the translational stop codon in luc was altered (original TAA to TAT) so translation will continue to the overlapping translational stop-start site. The pKO1celB plasmid (FIG. 4) was constructed by PCR amplification of the celB gene from pLB11 using the primers 5'-AGTCATGAA-CATATGCCCAGCATAA-3' (SEQ ID NO. 53) and 5'-ATG-GAATCATTTAATTAAATAGCCAGCGTT-3' (SEQ ID NO. 54) which introduced the NdeI and PacI restriction sites, respectively, for cloning purposes. Also, the translational stop codon in celB was altered (original TGA to TAT) so translation will continue to the overlapping translational stop-start site.

Construction of the Pm 5' Untranslated Transcript Mutant Libraries

It has previously been established that the ampicillin resistance level of host cells containing a plasmid-encoded β-lactamase gene (bla) is approximately proportional to the copy number of the plasmid (Uhlin and Nordstrom, 1977, Plasmid, 1, 1-7). Thus, ampicillin resistance can be used to estimate changes in the Pm promoter/5' untranslated transcript activity. The plasmids pLB1, pIB11, pKO1luc and pKO1celB were used for construction of mutant libraries (FIGS. 1 and 4). All these plasmids are based on the vector pJT19bla previously used in studies of Pm mutants (Winther-Larsen et al., 2000, supra). In the pLB1 and pIB11 constructs bla is a reporter of Pm activity. In the pKO1luc and pKO1celB plasmid bla is an indirect indicator of the expression of the first gene in the synthetic operon, luc and celB respectively. A kanamycin (Km) resistance gene allows for plasmid selection without the involvement of Pm for all the three constructs. To introduce mutations in the Pm 5' untranslated transcript region, a strategy involving synthetic oligonucleotides was used. Synthetic oligonucleotides were designed to constitute a double-stranded DNA fragment with the Pm 5' untranslated transcript sequence and AvrII- and NdeI-compatible ends when annealed, for subsequent easy cloning into the pLB1 vector. The synthetic oligonucleotides for cloning into the pIB11 and pKOluc, were designed to constitute a double-stranded DNA fragment with the Pm 5' untranslated transcript sequence and BspLU11I- and NdeI-compatible ends when annealed. For the pLB1 mutant library (LI) one of the oligonucleotides corresponded to the wild type Pm 5' untranslated transcript sequence (5'-TATGTTCATGACTCCATTAT-TATTGTACTAGTTGCATAAAGC-3') (SEQ ID NO. 55). The oligonucleotide corresponding to the other strand was randomly mutagenized by the use of a mixed oligonucleotide mix (5'-CTAGGCTTTATGCA23124123221221122144241321422CA-3' (SEQ ID NO. 56), where the numbers in the oligonucleotide indicate the doping percentages of the nucleotides: 1=4.8% A, 4.8% C, 4.8% G, 85.6% T; 2=85.6% A, 4.8% C, 4.8% G, 4.8% T; 3=4.8% A, 85.6% C, 4.8% G, 4.8% T; 4=4.8% A, 4.8% C, 85.6% G, 4.8% T). Two mutant libraries, called high (LII) and low (LIII), were made for pIB11 with different probability for mutational frequencies. Again one of the oligonucleotides corresponded to the wild type Pm 5' untranslated transcript sequence (5'-TATGTTCATGACTCCATTAT-TATTGTA-3') (SEQ ID NO. 57), and the oligonucleotide corresponding to the other strand was randomly mutagenized by the use of a mixed oligonucleotide mix (5'-CATGT1211411411433134214311CA-3' (SEQ ID NO. 58), where the numbers in the oligonucleotide indicate the doping percentages of the nucleotides. For the pIB11 high mutant library (LII) the doping percentages of the nucleotides are: 1=70% A, 10% C, 10% G, 10% T; 2=10% A, 70% C, 10% G, 10% T; 3=10% A, 10% C, 70% G, 10% T; 4=10% A, 10% C, 10% G, 70% T, and for the pIB11 low mutant library (LIII) the doping percentages of the nucleotides are: 1=79% A, 7% C, 7% G, 7% T; 2=7% A, 79% C, 7% G, 7% T; 3=7% A, 7% C, 79% G, 7% T; 4=7% A, 7% C, 7% G, 79% T). The pKO1luc (LIV) and pKO1celB (LV) mutant libraries were made in the same way as the pIB11 low mutant library described above.

Before annealing, a mix of 700 pmol of each of the oligonucleotides was phosphorylated by Polynucleotide Kinase (NEB). Subsequently NaCl was added to a final concentration of 200 mM and the phosphorylated oligonucleotides were annealed by gradual cooling from 95 to 20° C. during 30 min in a PCR machine. Dilutions of the resultant DNA fragments were ligated into AvrII- and NdeI-digested plasmid pLB1 or BspLU11I- and NdeI-digested plasmid pIB11, pKO1luc or pKO1celB. The digested plasmids had been dephosphorylated by Calf Intestinal Phosphatase (NEB) and purified by Qiaquick PCR purification kit (Qiagen) before ligation. The ligated plasmids were transformed into E. coli DH5α (pLB1 library), E. coli SuperGold competent cells (Stratagene) (pIB11 high and low mutant libraries) or E. coli Novablue Supercompetent cells (Novagen) (pKO1luc and pKO1celB mutant library) using the kanamycin resistance gene as a selection marker. For each library the obtained transformants were mixed and used as a library. Approximately 100 000 colonies was obtained in the transformation of pLB1 mutant library, 25 000 colonies for the pIB11 low mutant library, 75 000 colonies for the pIB11 high mutant library, 200 000 colonies for the pKO1luc mutant library and 300 000 colonies for the pKO1celB mutant library.

Screening for High Expression Pm 5' Untranslated Transcript Mutants and Determination of Ampicillin-resistance.

To identify mutants with increased expression from Pm 5' untranslated transcript region, a 1% aliquot of the mutant library was inoculated in 10 mL L-broth with kanamycin and inducer added to a concentration of 2 mM m-toluate. The culture was grown for approximately 4 hours and the cells were plated out at about 100 000 cells per plate on agar medium containing inducer and various ampicillin concentrations. The plates were incubated at 30° C. for approximately 40 hours and inspected for growth. Candidates growing at the highest ampicillin concentrations were then individually retested by the following procedure. Individual colonies were inoculated with 100 µL L-broth with kanamycin in 96-wells microtiter plates (Nunc). The cells were incubated at 30° C. overnight and diluted twice by a 96-pin replicator and microtiter plates with 100 µL L-broth in each well. Subsequently, the 96-pin replicator was used to plate the cells on L agar with or without inducer and various concentrations of ampicillin. The plates were incubated at 30° C. for approximately 40 hours before inspected for growth. The sequence of the Pm 5' untranslated transcript region was determined for the selected high expression candidates using the sequencing primer 5'-CTATCAAACCGGACACGTTTATCGTGGT-TATGC-3 (SEQ ID NO. 59). PCR product was used as template for the sequencing reaction generated with the primers 5'-CTTTCACCAGCGTTTCTGGGTG-3' (SEQ ID NO. 60) and 5'-GATGTAGAAAGGCGCCAAGTC-3' (SEQ ID NO. 61) for pLB1 and pIB11 generated mutants, the primers 5'-GATGTAGAAAGGCGCCAAGTC-3' (SEQ ID NO. 62) and 5'-TTCGAAGTATTCCGCGTACGTG-3' (SEQ ID NO. 63) for the pKO1luc generated mutants, and the primers 5'-GATGTAGAAAGGCGCCAAGTC-3'(SEQ ID NO. 64) and 5'-TGGTCAGCGAGGAACCACGATG-3' (SEQ ID NO. 65) for the pKO1celB generated mutants. All mutants reported under Results were reproduced by cloning annealed synthetic oligonucleotides with the mutations identified in the original isolate as described for the mutant libraries. *E. coli* DH5α was always used for the reproduction and in the further growth studies. Finally the Pm 5' untranslated transcript region of transformants was sequenced as described above.

Enzyme Assays

*E. coli* DH5α cells with the relevant plasmids were diluted 100-fold from an overnight culture grown in selective media into 13 mL L-broth with kanamycin added. The cultures were incubated at 37° C. until the cell density reached an optical density at 600 nm of 0.1. Then the cells were induced by m-toluate at a concentration of 2 mM, and further grown at 30° C. for 5 hours. (Except the cells with pLB9 plasmid which were diluted 100-fold from an overnight culture grown in selective media into 13 mL L-broth with kanamycin added, and grown at 30° C. for 6 hours.) Aliquots of cells were snap-frozen in a mixture of dry-ice and ethanol, and stored at −80° C. for subsequent assays. The method used for β-lactamase assay was a modified version of the method described by Chervaux et al. (1995, Mol. Gen. Genet., 249, 237-245), according to Winther-Larsen et al. (2000, supra). CelB activities were measured as described by Fjaervik et al. (1991, FEMS Microbiol. lett., 77, 325-330). A Lambda 35 UV/VIS spectrophotometer (Perkin Elmer instruments) was used for the enzymatic kinetic studies. Total protein concentrations were determined using PROTEIN ASSAY (Bio-Rad). Luc activities were measured as described by Blatny et al. (1997, Appl. Environ. Microbiol. 63, 370-379), using the luciferase assay system from Promega and a TD-20/20 luminometer (Turner Biosystems). All enzyme activity analyses were repeated at least two times. For all enzyme assays, measurements were carried out with three recurrences for each sample.

RNA Isolation, cDNA Synthesis, and Real-time PCR

*E. coli* DH5α cells with the relevant plasmids were grown as described for enzyme assays. For stabilization of the RNA, cell cultures were treated with RNAprotect (Qiagen) prior to freezing of cell pellets for subsequent RNA isolation. RNA was isolated using the RNAgeous kit (Ambion) as described by the manufacturers. The concentration and purity of the RNA was examined by determining the absorbance at 260 and 280 nm in a Lambda 35 UV/VIS spectrophotometer (Perkin Elmer instruments). The RNA preparations were treated with DNase (DNA-free, Ambion) to remove any contaminating DNA. cDNA was produced from 3 μg total RNA as template using the First-Strand cDNA synthesis kit (Amersham Biosciences) with random pd(N)$_6$ primers as described by the suppliers.

Real-time PCR was used for quantification of bla, luc, and celB transcripts. Primers were designed using the primer design program of Clone Manager version 6.0 (Scientific & Educational Software) to give products of approximately 250 base pairs (bp). Primer sequences used for Real-Time PCR are given in Table 2. The Power SYBR® Green PCR Master Mix (Applied Biosystems) was used for the Real-time PCR reactions, and the reactions were carried out in a 7500 Real Time PCR System instrument (Applied Biosystems). Optimal primer concentrations were determined for each primer set, and varied from 160 nM to 240 nM. Amplification for each sample was carried out in triplicate wells. The PCR cycles were as follows: 10 min at 95° C., followed by 40 cycles consisting of 15 sec at 95° C. and 60 sec at 60° C. Relative quantities were determined using the software of 7500 Real Time PCR System instrument. cDNA produced from cells carrying plasmids with the wt Pm was used as a calibrator (pIB11, pLB9, pKT1, pLB11 for bla, bla, luc, and celB, respectively). A fragment from the km resistance gene was used as a normalizer except for the cop271 mutant measurements where a fragment from the 16S rRNA gene was used as a normalizer.

mRNA Stability Measurements

*E. coli* DH5α cells with pLB9 plasmid were diluted 100-fold from an overnight culture grown in selective media into 13 mL L-broth with kanamycin added. The cultures were incubated at 30° C. and grown for approximately 5 hours. Rifampicin (Sigma) was added to a concentration of 200 μg/mL, which refers to time 0. Aliquots of 1 mL cell culture were withdrawn at the following time points: −1, 1, 3, 5, 7, 9 and 15 min. and snap-frozen in a mixture of dry-ice and ethanol. The samples were stored at −80° C. for subsequent RNA isolation, cDNA synthesis and Real time PCR as described above.

Results

Isolation of UTR Mutants Displaying Strongly Stimulated Expression from the Pm Promoter To simplify cloning of the oligonucleotide mixture covering the UTR region the plasmid pLB1 was constructed, in which the UTR could be cloned as AvrII/NdeI fragments (FIG. 1). *E. coil* DH5α transformants were selected on agar-medium containing kanamycin, pooled, and frozen as a stock culture. Exponentially growing cells from this stock culture were used for identification of UTR mutants by plating the cells on agar medium containing m-toluate and varying concentrations of ampicillin. Colonies growing at the highest concentrations of this antibiotic were picked and retested to confirm their phenotypes. The UTR regions were then sequenced and eleven of these mutants (LI-1 to LI-11, Table 3) were finally reproduced by resynthesizing both complementary strands for each of them, followed by annealing and cloning into the AvrII/NdeI sites of pLB1. In all cases the phenotypes were indistinguishable from the original isolates, confirming that the mutations in the UTR were causing these phenotypes.

Cells containing the wild-type UTR (pLB1) grew up to 30 μg/ml of ampicillin under uninduced conditions, and up to about 1 mg/ml in the presence of inducer. All the eleven mutants grew at concentrations ranging from 6 to 9 mg/ml of ampicillin under induced conditions, indicating a very strong stimulation of expression that appeared to be far above what was previously observed with Pm promoter mutants (Winther-Larsen et al., 2000, supra). Under uninduced conditions the stimulation of expression was much less prominent (up to a doubling of resistance relative to wild-type, Table 3). Inspection of the 11 mutant UTR sequences showed that they contained 3-6 point mutations, and that none of the sequences were identical (Table 3, part a). However, the distribution of the mutations is clearly not completely random. Most of the mutations are located in the 5' half of the sequence, and certain bases were much more frequently mutated than others. This is particularly clear for bases number 2 (A to C or T), 3 (C to A), 12 (T to C) and 14 (A to C or T) from the 5' end in the sequence displayed in the Table. Further, base numbers 4 and 7 were never changed, and bases downstream of number 17 were not changed with the exception of two nucleotides (mutants LI-1 and LI-11, respectively). At least some of the core bases putatively involved in ribosome-binding (GGAG) were not changed in any of the mutants.

Many of the mutants (LI-1 is a clear exception) carried changes near the previously determined transcriptional start site. A new library was further constructed in which mutations were introduced only from base number 8 from the assumed transcriptional start site and further downstream to the NdeI site. For this experiment a slightly modified plasmid construct (pIB11) was used in which bases number 4 and 5 from the 5'end were changed from TA to AT, generating a BspLU111 site (FIG. 1). The purpose of making this modification was to simplify transfer of mutant UTR regions into another construct that was used in parallel to study promoter mutations. Two UTR libraries (LII and LIII) were made in this construct, one with a higher (LII) frequency of mutations introduced at the oligonucleotide synthesis step. Both pIB11 libraries were screened as described above for pLB1, and the UTR regions of 16 sequenced mutants were finally resynthesized (LIII-13 and LIII1-3, Table 3, part b). Cells containing wild-type pIB11 displayed a phenotype that was quite similar to that of pLB1, and the expression of the pIB11 mutants appeared to be equally strongly stimulated as in the pLB1 mutants. Generally, the expression levels under uninduced conditions were higher than in the LI library. As for the pLB1 mutants each pIB11 mutant contained several different mutations (2-5), and as expected they were all located downstream of the first base to be mutagenized. All mutants were different, but certain base changes were again over-represented, such as at positions 10 (A to C), 24 (C to A or T) and 25 (A to T, C in one case). In mutant LII-12 there was only one base substitution (A to C), but this particular mutant lost two bases at positions 24 and 27. Further, among all the 52 base-substitutions taking place in this library, not a single one introduces a G (2 out of 48 in the pLB1 mutants).

The Mutants Stimulate Expression Both at the Transcriptional and Translational Levels The very strong increases in ampicillin resistances displayed by the mutants were assumed to be a direct result of enhancement of β-lactamase production, but it could not be concluded from these data whether the stimulation was caused by transcriptional or translational effects. β-lactamase activities and corresponding transcript levels for 7 of the 13 mutants in the LII and LIII library were therefore measured (FIG. 2, panel a). At the enzyme level the factor of stimulation was as high as up to a factor of 20 (LII-11), relative to wild-type. This is an unexpectedly high number taking into consideration that the wild-type system has been shown to be useful for industrial levels of production of a recombinant protein (Sletta et al., 2004, Appl. Environ. Microbial., 70, 7033-7039). Even more surprising was the observation that transcription was also strongly stimulated (a factor of about 8 for LII-11).

The mutations in libraries I and II are not located near the transcriptional start site. The start sites for LII-11 and LII-13 were determined by primer extension analysis. The results showed that the transcriptional start sites were the same for these two mutants and identical to that of the wild-type (data not shown). The results obtained with the UTR mutants therefore lead to the unexpected conclusion that in order to stimulate the transcript levels of a recombinant gene it may be equally efficient to mutate the UTR as to mutate the promoter.

The UTR Mutations also Stimulate the Expression from an Alternative Promoter, $P_{antitet}$ The Pm promoter in pIB11 was exchanged with the constitutive $P_{antitet}$ promoter, as described in the Methods Section. The UTR in the resulting plasmid, designated pLB9, was then exchanged with those present in the mutants used for measurement of transcription and translation (see above). Analyses of the bla expression levels (induced) from the corresponding plasmids showed that all these mutants were also strongly stimulating expression from Pantitet. (FIG. 2, panel b), and the results were also quite similar at the transcriptional level. Even though the levels of stimulation are on average slightly lower in the Pantitet context, the main conclusion is that the UTR mutations to a large extent act independent of the upstream promoter sequence.

The strong stimulation of the amount of transcripts present could in principle be caused either by the production of more transcripts per unit of time by RNA polymerase, or it could be the result of increased transcript stability. To distinguish between these two possibilities the decay of already produced bla mRNA was followed as a function of time in the presence of rifampicin, which inhibits initiation of transcription (FIG. 3). mRNA from mutants LII-11 and LII-13 were used in these studies, and the experiments showed that the decay rates were significantly slower for both mutant mRNAs than for the wild-type mRNA. Using the time required to reach 50% decay as a criterion for stability the data indicate that the mutant mRNAs are at least three times more stable than those of the wild-type. Therefore, these data indicate that at least some of the stimulatory effect is a result of enhanced mRNA stability.

The UTR Mutants also Stimulate the Expression of Two other Reporter Genes (luc and celB), but not to the Same Extent as for bla The eukaryotic luc gene (encoding firefly luciferase) is expressed in small quantities, presumably at least partly due to a codon usage that is suboptimal for this host. The bla gene in pIB11 was substituted with luc, generating pKT1, and each of the seven mutant UTR sequences (see above) were then introduced such that their effects on luc expression could be evaluated. The stimulatory effects were much smaller than for bla, and for three of the mutants, expression was unchanged (LII-8, LIII-3) or lower (LII-13) than in the wild-type at the enzyme level (FIG. 2, panel c). The highest expression (LII-12) was around a factor of two higher than from the plasmid with wild-type UTR. Interestingly, at the mRNA level expression was generally more stimulated than at the protein level (see particularly LII-10), while the opposite was true for bla expression.

celB encodes phosphoglucomutase from Acetobacter xylinum, and has, in contrast to luc, previously been shown to be expressed at unusually high levels from Pm in E. coli (Blatney et al., 1997, supra). As described for luc the bla gene in pIB11 was substituted with celB, generating pLB11, and the effects of the UTR mutants on celB expression were then evaluated (FIG. 2, panel d). The results of these experiments were strikingly similar to the corresponding experiments with luc, in that the stimulation was generally much lower (or non-existent) than for bla, but stronger at the transcriptional than at the protein activity level.

Construction of a Synthetic Operon for Easy Selection of UTR Mutants Stimulating Expression of Any Gene Although it appeared very probable that the expression of luc and celB were limited by other parameters than the UTR sequence, it seemed possible that the enormous stimulation achieved with bla was partly a result of the screening method itself. This means that the UTR mutations could to some extent be particularly well adapted to the downstream coding sequence of bla. To analyze this a new plasmid (pKO1) was constructed, in which any gene can be inserted downstream of Pm, but where bla is inserted as the second gene in such a way that its translation is directly coupled to the translation of the upstream gene through overlapping stop and start sites (FIG. 4). This process is known as translational reinitiation and is caused by the supposed bidirectional mRNA movement of the ribosome after translational termination, depending on the neighboring sequences, when the translational stop codon partially overlaps (e.g. UA<u>AUG</u>) or is close in space to a start codon. The luc gene was then inserted, generating pKO1luc, and the doped oligonucleotide mixture used to generate library LIII was then also used to construct a new UTR library (LIV) in pKO1luc. This library was screened for high-level resistance to ampicillin, as described above, and four mutants (LIV-1, -2,-3 and -4) were selected for further studies. The sequences of the UTR regions in these mutants were determined (Table 3), resynthesized and cloned into pKT1 as above. Two of the mutants (LIV-1 and 2) carried single insertions, a G for LIV-1 and a T for LIV-2. No insertions were observed in any of the previous screens and introduction of a G was very rarely observed. In addition, a new G was present also in LIV-4. In LIV-1 the A at position 10 was substituted by a T, while it was consistently changed to a C in the LII mutants. The patterns of changes therefore generally appeared to be different from those found when the screening was done without luc as an upstream gene.

The expression levels of luc were then measured in the respective pKT1 derivatives (FIG. 5, panel a), and interestingly, all these four mutant UTR sequences stimulated expression similar to or better than the best mutant identified in the LII and LIII library, LII-12 (FIG. 2, panel c).

The wild-type UTR of pIB11, used to isolate the LII and LIII mutants was substituted with each of the mutants LIV-1 to LIV-4. The β-lactamase activities were then measured under induced conditions, and the results clearly showed that although these mutations also stimulated bla expression (FIG. 5, panel b), the stimulation was much weaker than for the corresponding LII mutants (FIG. 2, panel a). There was also a very significant variability in the levels of stimulation by the LIV mutants, ranging from a factor of about 3 (LIV-3) to a factor of about 11 (LIV-2). At the transcriptional level the difference from the LII mutants was also striking, as the amounts of LIV mutant transcripts to a greater extent correlated with the level of protein product.

As stated above the celB gene is very strongly expressed from Pm, and the LII and LIII mutants did not stimulate expression of this gene more than about 50% (FIG. 2, panel d). celB was cloned as gene 1 in the pKO1 construct (as described above for luc), generating pKO1celB. This library (LV) was again screened for high-level resistance to ampicillin, and selected mutants were sequenced, resynthesized and the wild-type UTR in pIB11 was then substituted with these mutants (LV-1 to LV-4). The mutations were again different from any of those previously isolated, but unlike for LIV, no insertions or Gs had been introduced. Nucleotides 17 and/or 18 were changed in all LV mutants, and this was also the case in 3 of the 4 LIV mutants. Measurements of expression at the protein level (FIG. 5, panel c), showed that 3 of the 4 mutants stimulated expression with about 50%, similar to the best mutant, LII-10, from the LII and LIII library (FIG. 2, panel d). At the transcriptional level stimulation was significantly stronger in 3 of the four mutants. The pIB11 construct was also tested by introducing the trfAcop271 mutation, and in agreement with the previously reported results the expression level increased correspondingly at both the transcriptional and translational levels (FIG. 5, panel c).

If the stimulation of celB expression by the LV mutants is mostly a result of transcriptional stimulation one might envision that these mutants would be more stimulatory to bla expression than the LIV mutants. This was tested by exchanging the wild-type UTR in pIB11 with each of the 4 LV mutants, and interestingly, all four mutations quite strongly stimulated bla expression (a factor of about 13 to about 19). Furthermore, this stimulation was much stronger than the expected stimulation (a factor of 4-5) obtained by introducing the trfAcop271 mutation into wild-type pIB11. Consistent with these data was the observation that in contrast to celB, bla gene expression was stimulated by a similar factor at the transcriptional as at the product level (FIG. 5, panel d).

TABLE 1

| Bacterial strains and plasmids | | |
|---|---|---|
| Bacterial strain or plasmid | Properties* | Source of reference |
| E. coli DH5α | endA1, hsdR17, supE44, thi-1, λ, recA1, gyrA96, relA1, lacU169 (80dlacZ, M15) | Bethesda Research Laboratories |
| E. coli NovaBlue | endA1, hsdR17($r_{K12}^-$, $m_{K12}^+$), supE44, thi-1, recA1, gyrA96, relA1, lac, F'[proA+B+, lacI<sup>q</sup>ZΔM15::Tn10(Tc<sup>R</sup>)] | Novagen |
| E. coli SoloPack Gold | Tc<sup>r</sup>, Δ(mcrA)183, Δ(mcrCB-hsdSMR-mrr)173, endA1, supE44, thi-1, recA1, gyrA96, relA1, lac, Hte [F' proAB lacI<sup>q</sup>ZΔM15 Tn10 (Tc<sup>r</sup>) Amy Cm<sup>r</sup>] | Stratagene |
| pJT19bla | RK2-based expression vector containing the Pm promoter with the gene encoding the regulatory protein XylS and bla as a reporter gene for Pm and. Km<sup>r</sup>. 8.1 kb. | Winther-Larsen et al. (2000) |
| pIB6 | A pJT19bla derivative in which a XbaI/MunI fragment containing rrnBT1T2 was cloned into the same sites of pJT19bla. A translational down-mutation in the Pm 5' untranslated transcript region is inserted. An AflIII site is introduced upstream the Pm promoter and a BspLU11I restriction site is inserted downstream the Pm transcriptional start site. Km<sup>r</sup>. 8.1 kb | Bakke et al. (2006) |
| pIB11 | A pIB6 derivate where the translational down mutation in the Pm untranslated transcript sequence is changed back to wild type (GAAG to GGAG). Km<sup>r</sup>. 8.1 kb. | This study |

TABLE 1-continued

Bacterial strains and plasmids

| Bacterial strain or plasmid | Properties* | Source of reference |
|---|---|---|
| pTA8 | A pJT19bla derivative in which the NcoI site in the xylS gene is eliminated and an AgeI restriction site is inserted downstream of the xylS gene. Km$^r$. 8.1 kb | Unpublished results |
| pLB1 | A pTA8 derivative in which an AvrII restriction site is inserted upstream of the Pm transcriptional start site. Km$^r$. 8.1 kb. | This study |
| pJT19luc | RK2-based expression vector containing the Pm promoter with the gene encoding the regulatory protein XylS and luc as a reporter gene for Pm Km$^r$. 8. kb. | Winther-Larsen et al (2000) |
| pKT1 | A pIB11 derivative where the NdeI/BamHI fragment containing bla was substituted with an NdeI/BamHI fragment containing luc from pJT19luc. Km$^r$. 8.8 kb. | This study |
| pJB658celB | Derivative of pJB658 with celB cloned in the NdeI site downstream of Pm. Km$^r$. 8.7 kb. | Blatny et al. (1997) |
| pLB11 | A pIB11 derivative where the NdeI/BamHI fragment containing bla was substituted with the NdeI/BamHI fragment containing celB from pJB658celB. Km$^r$. 9.0 kb. | This study |
| pBR22 | Plasmid with rep replicon. Ap$^r$. 4.4 kb. | NEB |
| pLB9 | A pIB11 derivative where the XbaI/BspLU11I fragment containing the Pm promoter and start of xylS is substituted with the P$_{anti-tet}$ promoter from pBR322. Km$^r$. 7.4 kb. | This study |
| pKO1 | A pIB11 derivative in which a Km$^r$. 8.1 kb. | This study |
| pKO1luc | A pKO1 derivative with luc cloned in the NdeI/PacI site downstream of Pm Km$^r$. 9.8 kb | This study |
| pMAMA5-Arg5 | A plasmid used for obtaining the tRNA$^{Arg5}$ gene. | Lopez et al. (1994) |
| pLB11Arg5 | A pLB11 derivative carrying the tRNA$^{Arg5}$ gene from pMAMA5-Arg5 in the BamHI site. Km$^r$. 9.1 kb. | This study |
| pK18mob | A plasmid that facilitated an intermediate cloning for bla. | Schäfer et al. (1994), Gene, 145, 69-73 |
| pK18mob-bla | A pK18mob derivative where the XbaI/BamHI fragment carrying the bla from pIB11 was cloned into the multiple cloning site. Km$^r$. 4.8 kb. | This study |
| pLB11blaArg5 | A pLB11Arg5 derivative in which the NdeI/SalI fragment containing celB was substituted with the NdeI/SalI fragment containing bla from pK18mob-bla. Km$^r$. 8.0 kb. | This study |

Ap$^r$, ampicillin resistance;
Cm$^r$: Chloramphenicol resistance;
Km$^r$, kanamycin resistance;
Tc$^r$: tetracycline resistance

TABLE 2

Primers used for Real-Time PCR.

| Target gene | Sequence |
|---|---|
| bla | 5'-ACGTTTTCCAATGATGAGCACTT-3' (SEQ ID NO. 66) |
| bla | 5'-TGCCCGGCGTCAACAC-3 (SEQ ID NO. 67) |
| luc | 5'-CGGCGCCATTCTATCCTCTA-3' (SEQ ID NO. 68) |
| luc | 5'-AGGGCGTATCTCTTCATAGCCTTAT-3' (SEQ ID NO. 69) |
| celb | 5'-ACCAGCTTCAATGAAAACCACAT-3' (SEQ ID NO. 70) |
| celb | 5'-CGCCCTTGCGGTAATCG-3' (SEQ ID NO. 71) |
| Km | 5'-TACCTTTGCCATGTTTCAGAAACA-3' (SEQ ID NO. 72) |
| Km | 5'-AATCAGGTGCGACAATCTATCGA-3' (SEQ ID NO. 73) |
| 16S rRNA | 5'-ATTGACGTTACCCGCAGAAGAA-3' (SEQ ID NO. 74) |
| 16S rRNA | 5'-GCTTGCACCCTCCGTATTACC-3' (SEQ ID NO. 75) |
| tRNA$^{Arg5}$ | 5'-GTCCTCTTAGTTAAATGG-3' (SEQ ID NO. 84) |
| tRNA$^{Arg5}$ | 5'-AGGAATCGAACCTGC-3' (SEQ ID NO. 85) |

TABLE 3

Summary of the high level expression mutants identified in all of the Pm 5' untranslated transcript mutant libraries.

| Name | SEQ ID NO: | Sequence of the Pm 5' untranslated transcript region[6] | Ampicillin concentration[7] [μg/mL] | |
|---|---|---|---|---|
| | | | Uninduced | Induced with 2 mM m-toluate |
| a)[1] | | | | |
| pLB1 wild type | 1 | Aactagtacaataataatggagtcatgaacatatg | 30 | 800-1000 |
| LI-1 | 2 | ........t..c.c.........c............ | 20 | 6500-7500 |
| LI-2 | 3 | .ca......t.....t................... | 3-40 | 6000-6500 |
| LI-3 | 4 | .ca.t....t.....g................... | 40-60 | 6500 |
| LI-4 | 5 | .ta........c.....c.................. | 40-60 | 6000-6500 |
| LI-5 | 6 | .ta..c.....c.t..................... | 60 | 6000-6500 |
| LI-6 | 7 | ...a.t.....c......c................ | 40-60 | 6000-6500 |
| LI-7 | 8 | .t......t..c.ta.................... | 60 | 7000 |
| LI-8 | 9 | .ca..........t..................... | 60 | 6000-6500 |
| LI-9 | 10 | .t.....gt..c.ta.................... | 60 | 8000-9000 |
| LI-10 | 11 | ..a......c.c.c..................... | 60 | 7500 |
| LI-11 | 12 | ..a.......c...c..........a......... | 60 | 6000 |
| b)[2] | | | | |
| pIB11 wild type[3] | 13 | ...at.............................. | 10 | 1000 |
| LII-1 | 14 | .........c.......a......t.......... | >400 | 6000 |
| LII-2 | 15 | .........c.............tt.......... | 100 | 7000 |
| LII-3 | 16 | .........c...t..........t.......... | 100 | 7000 |
| LII-4 | 17 | .........c.............a........... | 200 | 6000-7000 |
| LII-5 | 18 | .......ca..c.c.........a........... | 200 | 6000 |
| LII-6 | 19 | ........ac.............t........... | 200 | 7000 |
| LII-7 | 20 | ........ac.....c......a........... | 100 | 6000-7000 |
| LII-8 | 21 | .........c.c............t.......... | 100-200 | 8000 |
| LII-9 | 22 | ..........c...ca........c......... | 200 | 7000 |
| LII-10 | 23 | .........c.c...........tt.......... | 100 | 8000 |
| LII-11 | 24 | .......tac.c..........a........... | 100 | 8000-9000 |
| LII-12 | 25 | ........c...............-..-...... | 100 | 8000 |
| LII-13 | 26 | ........c.c..t....c.......t........ | 100 | 7000-8000 |
| LIII-1 | 27 | .........c..............c.......... | 100 | 6000 |
| LIII-2 | 28 | .........c...t..........t.......... | 1000 | 6000 |
| LIII-3 | 29 | .........c..............t.......... | 100 | 7000-8000 |
| c)[4] | | | | |
| LIV-1 | 30 | .........t........c...[g]........... | 20-40 | 3000-4000 |
| LIV-2 | 31 | .......[t].........tt.....c.......... | 60-80 | 9000-10000 |
| LIV-3 | 32 | ...............cac................. | 20 | 4000-5000 |

TABLE 3-continued

Summary of the high level expression mutants identified in all of the Pm 5' untranslated transcript mutant libraries.

| Name | SEQ ID NO: | Sequence of the Pm 5' untranslated transcript region[6] | Ampicillin concentration[7] [μg/mL] Uninduced | Ampicillin concentration[7] [μg/mL] Induced with 2 mM m-toluate |
|---|---|---|---|---|
| LIV-4 d)[5] | 33 | .......c...gt...ca................ | 20 | 4000-5000 |
| LV-1 | 34 | .........c..t....c.....a.......... | 60-100 | 8000-9000 |
| LV-2 | 35 | .........c......ca.....t.......... | 80-100 | 11000 |
| LV-3 | 36 | ................ca...aca.......... | 60-100 | 9000 |
| LV-4 | 37 | ............c...cca....a.......... | 60-80 | 10000 |

[1] High level expression mutants identified in the pLB1 mutant library (LI)
[2] High expression mutants identified in the pIB11 high (LII) and low (LIII) mutant libraries.
[3] The wild-type plasmid is pIB11 also for the LIV (c) and LV (d) mutants in this table.
[4] High level expression mutants identified in the pKO1luc mutant library (LIV).
[5] High level expression mutants identified in the pKO1celB mutant library (LV).
[6] Short horizontal lines in the sequence mean that the corresponding nucleotides are missing in the corresponding mutant. Nucleotides in superscript in the sequence mean insertion of this nucleotide at this point in the sequence in the corresponding mutant
[7] All the mutants are reproduced with bla as the reporter gene to the Pm promoter, which means that plasmid pLB1 or pIB11 are used, and the concentrations of ampicillin refer to the maximum levels tolerated by each mutant under uninduced and induced conditions grown on L-agar.

TABLE 4

| SEQ ID No. | Sequence of the Pm 5' translated transcript region[6] |
|---|---|
| 1 | Aactagtacaataataatggagtcatgaacatatg |
| 2 | ........t..c.c........c............ |
| 3 | .ca.......t.....t.................. |
| 4 | .ca.t....t.....g................... |
| 5 | .ta........c....c.................. |
| 6 | .ta..c.....c.t..................... |
| 7 | ...a.t....c........c............... |
| 8 | .t......t..c.ta.................... |
| 9 | .ca..........t..................... |
| 10 | .t.....gt..c.ta.................... |
| 11 | ..a.....c.c.c...................... |
| 12 | ..a.....c..c........a.............. |
| 13 | ...at.............................. |
| 14 | ........c......a......t............ |
| 15 | ........c..........tt.............. |
| 16 | ........c..t..........t............ |
| 17 | ........c..............a........... |
| 18 | .......ca..c.c........a............ |
| 19 | ........ac............t............ |
| 20 | .......ac.....c......a............. |
| 21 | ........c.c...........t............ |
| 22 | ............c...ca........c........ |
| 23 | ........c.c..........tt............ |
| 24 | .......tac.c.........a............. |
| 25 | ........c.............-...-........ |
| 26 | .......c.c..t...c......t........... |
| 27 | .........c..............c.......... |
| 28 | ........c...t........t............. |
| 29 | .........c...........t............. |
| 30 | ........t.......c...[g]............ |
| 31 | .......[t].........tt.....c.......... |
| 32 | ................cac................ |
| 33 | .......c...gt...ca................. |
| 34 | .........c..t....c.....a........... |
| 35 | .........c......ca.....t........... |
| 36 | ................ca...aca........... |
| 37 | ............c...cca....a........... |

EXAMPLE 2

Experiments Designed to Show that UTR Mutants Stimulate Expression by Enhancing Transcription
Use of tRNA$^{Arg5}$ Gene as a Transcriptional Reporter The principle underlying the test results described below is as follows: The bla gene is transcriptionally fused to the tRNA$^{Arg5}$ gene sequence, encoding a rare *Escherichia coli* arginine isoacceptor. Since it is generally accepted that tRNA is stable in the cell, the presence of more of it in UTR mutants (compared to wild-type UTR) would indicate that more tRNA has been produced by the mutant (Lopez et al. 1994, Nucleic Acids Research 22(7), 1186-1193). The tRNA$^{Arg5}$ gene is thus used as indicator of increased transcript production (i.e. as a transcriptional reporter). Since bla mRNA is expected to have a much faster turnover, an observed increase in the amount of bla mRNA transcript might be the result of increased stability of the mutant UTR RNA. The same cannot be true for the tRNA since it is generally stable, and since the tRNA originates from the same transcript as bla it follows from an increase in the tRNA gene transcript that more bla transcript must also have been produced. If the observations were to be explained by increased stability, the tRNA of the mutants would be approximately the same as for wild-type. The amount of transcript is measured by quantitative Real-Time PCR.

Plasmid Construction
Cloning of the tRNA$^{Arg5}$ Gene as a BamHI Fragment.

The tRNA$^{Arg5}$ gene was PCR amplified from plasmid pMAMA5-Arg5 by using primers that introduce restriction sites for BamHI as mismatch (5'-CAGTAATTTCGAgGATCcGCATTGTC-3' (SEQ ID NO. 80) 5'-AAggATCCGCGCGCGACCA-3' (SEQ ID NO. 81). BamHI sites are underlined, and mismatches are indicated as lowercase). The BamHI digested PCR-fragment was then cloned into the BamHI site downstream of the celB gene in pLB11, generating plasmid pLB11Arg5.

Construction of pLB11blaArg5, Expressing a Fused bla-tRNA$^{Arg5}$ Transcript from Pm.

The XbaI/BamHI fragment from pLB11 carrying the bla gene was cloned into the multiple cloning site of vector pK18mob, leading to pK18mob-bla. The bla gene was then PCR amplified from pK18mob-bla by using the primers 5'-GGATGTGCTGCAAGGCGATT-3' (SEQ ID NO. 82), and 5'-ctgtgtcGACAGTTACCAATGCTTAAT-3' (SEQ ID NO. 83), which introduce the restriction site for SalI for cloning purposes (SalI site is underlined and mismatches are indicated as lowercase). An NdeI/SalI digested PCR product containing bla was then ligated into the NdeI/SalI partially digested pLB11Arg5. By this cloning the celB gene was substituted with bla, generating the plasmid pLB11blaArg5 (FIG. 6). In this construct bla and tRNA$^{Arg5}$ are transcriptionally fused. The construct also allows monitoring of the bla expression level by simply measuring the level of ampicillin resistance or the β-lactamase activity, as described elsewhere. The wild-type UTR in pLB11blaArg5 was finally substituted with UTR mutants LV-1 and LV-2 (Table 3), resulting in pLB11blaArg5LV-1 and pLB11blaArg5LV-2. To access the possible influence of tRNA$^{Arg5}$ fusion to bla, ampicilin resistance were detected compared to the constructs without tRNA$^{Arg5}$ fusion. Results are represented in the Table 5.

Quantitative Real-time PCR

By using specific primers for bla and tRNA$^{Arg5}$, respectively, each part of the fused transcript could be quantified after Pm induction of pLB11blaArg5, pLB11blaArg5LV-1 and pLB11blaArg5LV-2. The experiments were carried out by using qPCR with 16S rRNA gene as an endogenous control (Table 6). Primers that were used for the qPCR are listed in Table 2.

TABLE 5

Ampicillin resistance chart

| | Maximum ampicillin concentration [μg/mL] tolerated by host* | |
|---|---|---|
| Name | Uninduced | Induced with 2 mM m-toluate |
| pLB11blaArg5 | 10 | 1000 |
| pLB11blaArg5LV-1 | 100 | >12000 |
| pLB11blaArg5LV-2 | 100 | >12000 |

*The next higher concentration tested was the double of the one indicated as the limit, except for 12000, which was the highest tested.

TABLE 6

Transcription profile of pLB11blaArg5 constructs

| | Name | | | | | | | |
|---|---|---|---|---|---|---|---|---|
| | WT | | | LV-1 | | | LV-2 | |
| Target gene | min | | max | min | | max | min | max |
| bla | 0.877 | 1.000 | 1.141 | 10.244 | 11.744 | 13.463 | 11.928 | 14.282 | 17.101 |
| tRNA$^{Arg5}$ | 0.331 | 1.000 | 3.022 | 11.692 | 14.557 | 18.124 | 8.677 | 15.042 | 26.075 |

The invention claimed is:

1. A method of producing a desired heterologous gene product in a prokaryotic expression system, said method comprising expressing a gene encoding said heterologous gene product from a promoter at a level of at least 1% of the total cellular protein in a prokaryotic host cell using a mutant Pm mRNA leader having a sequence selected from any one of SEQ ID NOs 2-12 and 14-37.

2. The method of claim 1 wherein expression of the gene product is enhanced as compared to the level of expression obtained with the corresponding unmutated Pm mRNA leader in transcription of the gene.

3. The method of claim 1 wherein said promoter is selected from any one of a Pm promoter, a Ptac promoter, a PtrcT7 RNA polymerase promoter, $\lambda P_L$ or a $P_{BAD}$ promoter.

4. The method of claim 3 wherein said promoter is a Pm promoter.

5. The method of claim 1 wherein a vector comprising a strong promoter, a DNA region corresponding to said mutant Pm mRNA leader and said gene encoding said desired heterologous gene product is introduced into a prokaryotic host cell and said host cell is cultured to allow said gene to be expressed.

6. The method of claim 5 wherein said host cell is a bacterial cell.

7. A Pm mRNA leader sequence having a sequence selected from any one of SEQ ID NOs 2-12 and 14-37.

8. A vector comprising the Pm mRNA leader sequence of claim 7.

9. A library comprising the Pm mRNA leader sequence of claim 7.

10. A method of identifying an mRNA leader mutant which increases production of transcripts per unit of time of a desired gene as compared to production of transcripts per unit of time obtained with the corresponding unmutated leader, said method comprising: providing a vector comprising a promoter, a said desired gene under the control of said promoter and a reporter gene, wherein translation of the reporter gene is coupled to the translation of the desired gene; introducing a DNA sequence corresponding to said mRNA leader mutant into said vector upstream of said desired gene; introducing said vector into a prokaryotic host cell; and determining production of transcripts per unit of time of said reporter gene.

11. The method of claim 10 wherein said reporter gene is an antibiotic resistance gene.

12. The method of claim 11 wherein said reporter gene is bla.

* * * * *